United States Patent
Pachon Mateos et al.

(10) Patent No.: US 8,216,228 B2
(45) Date of Patent: *Jul. 10, 2012

(54) APPARATUS AND METHODS FOR ARRHYTHMIA TREATMENT BASED ON SPECTRAL MAPPING DURING SINUS RHYTHM

(75) Inventors: Jose Carlos Pachon Mateos, Moema-Sao Paulo (BR); Enrique Indalecio Pachon Mateo, Moema-Sao Paulo (BR)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 12/910,424

(22) Filed: Oct. 22, 2010

(65) Prior Publication Data

US 2011/0060327 A1 Mar. 10, 2011
US 2011/0301586 A2 Dec. 8, 2011

Related U.S. Application Data

(63) Continuation of application No. 11/202,049, filed on Aug. 11, 2005, now Pat. No. 7,819,862.

(51) Int. Cl.
*A61B 18/12* (2006.01)
*A61B 18/14* (2006.01)
(52) U.S. Cl. .......................... 606/41; 606/32
(58) Field of Classification Search ............. 600/374; 606/32, 41
See application file for complete search history.

(56) References Cited

U.S. PATENT DOCUMENTS

| | | | |
|---|---|---|---|
| 6,308,093 B1 | 10/2001 | Armoundas et al. |
| 6,370,412 B1 | 4/2002 | Armoundas et al. |
| 6,658,285 B2 | 12/2003 | Potse et al. |
| 7,123,954 B2 | 10/2006 | Narayan |
| 2005/0288599 A1 | 12/2005 | MacAdam et al. |

OTHER PUBLICATIONS

Kocovic et al., "Alterations of Heart Rate and of Heart Rate Variability After Radiofrequency Catheter Ablation of Supraventricular Tachycardia. Delineation of Parasympathetic Pathways in the Human Heart," Circulation 1993; 88; 1671-1681 (Oct. 1993).
Pachon, JC et al., "A New Curative Treatment for Paroxysmal Atrial Fibrillation (PAF) using the Fourier Right-Shift to Guide the RF-Ablation", *Europace* vol. 6, Suppl 1 Jun. 2004, Abstract.
Sutton R. How and when to pace in vasovagal syncope. J Cardiovasc Electrophysiol. Jan. 2002; 13(1 Suppl):S14-6.
Sutton R. Has cardiac pacing a role in vasovagal syncope? J Intery Card Electrophysiol. Oct. 2003; 9(2):145-9.
Benditt DG, Sutton R, Gammage MD, et al. Clinical experience with Thera Dr rate-drop response pacing algorithm in carotid sinus syndrome and vasovagal syncope. The International Rate-Drop Investigators Group. Pacing Clin Electrophysiol 1997, 20:832-839.

(Continued)

*Primary Examiner* — Lee Cohen
(74) *Attorney, Agent, or Firm* — Wiley Rein LLP

(57) ABSTRACT

Apparatus, methods, and computer-readable media herein described, depicted and claimed are applied for curative ablation to achieve the inactivation or destruction of fibrillar myocardium of so-called AF nests or other arrhythmogenic foci within the myocardial substrate. In addition, fibrillar myocardium may be identified and mapped by spectral analysis and phase study of the tissue during sinus rhythm. The procedure may be performed by transseptal puncture using only one catheter for ablation and mapping. The apparatus, methods, and computer-readable media may be used to localize the application targets even during an arrhythmia.

40 Claims, 21 Drawing Sheets

OTHER PUBLICATIONS

Kurbaan AS, Franzen AC, Heaven D, Mathur G, Bowker TJ, Petersen M, Sutton R Cardioinhibition during tilt testing identifies patients who may benefit from pacing. Pacing Clin Electrophysiol. Nov. 2000; 23(11 Pt 2):1792-4.

Connolly SJ, Sheldon R, Thorpe KE, Roberts RS, Ellenbogen KA, Wilkoff BL, Morillo C, Gent M; VPS II Investigators. Pacemaker therapy for prevention of syncope in patients with recurrent severe vasovagal syncope: Second Vasovagal Pacemaker Study (VPS II): a randomized trial. JAMA. May 7, 2003; 289(17):2224-9.

Geis WP, Kaye MP, Randall WC. Major autonomic pathways to the atria and S-A and A-V nodes of the canine heart. Am J Physiol. 1973; 224:202-208. [Medline].

Lazzara R, Scherlag BJ, Robison MJ, Samet P. Selective in situ parasympathetic control of the canine sinoatrial and atrioventricular nodes. Circ Res. 1973; 32:393-401. [Medline].

Billman GE, Hoskins RS, Randall DC, Randall WC, Hamlin RL, Lin YC. Selective vagal postganglionic innervation of the sinoatrial and atrioventricular nodes in the non-human primate. J Auton Nery Syst. 1989; 26:27-36. [Medline].

Randall WC, Milosavljevic M, Wurster RD, Geis GS, Ardell R. Selective vagal innervation of the heart. Ann Clin Lab Sci. 1986; 16:198-208. [Medline].

Chiou CW, Eble JN, Zipes DP—Efferent vagal innervation of the canine atria and sinus and atrioventricular nodes. The third fat pad. Circulation. Jun. 3, 1997; 95(11):2573-84.

Guyton AC, Hall JE. The Autonomic Nervous System. The Adrenal Medulla. In: Textbook of Medical Physiology, 9th ed. 1996, W.B. Saunders Company; 769-781.

Pachon M JC, Pachon M EI, Pachon M JC, Pachon MZC, Lobo TJ, Albornoz RN, Sousa LCB, Jatene AD—A New Curative Treatment for Paroxysmal Atrial Fibrillation (PAF) Using the Fourier Right-Shift to Guide the RF-Ablation. Europace, vol. 6 Suppl 1, Jun. 30, 2004.

Randall WC, Armour JA. Gross and microscopic anatomy of cardiac innervation. In: Randall WC, ed. Neural Regulation of the Heart. New York, NY: Oxford University Press; 1977:13-41.

Pachon M JC, Pachon M EI, Pachon M JC, Lobo TJ, Pachon MZC, Vargas RNA, Pachon DQV, Molina FJL, Jatene AD—A New Curative Treatment for Paroxysmal Atrial Fibrillation (PAF) Using the Fourier Right-Shift to Guide the RF-Ablation. HeartRhythm 1:1S,May 2004, S67/207.

Pachon JC, Pachon EI, Pachon J, Lobo TJ, Pachon MZC, Albornoz RN, Jatene AD: A New Treatment of Neurocardiogenic Syncope (NCS) and/or Functional AV Blocks (FAVB) with RF-Ablation. Europace vol. 6 (Suppl), Jm12004, 49.

Arrowood JA, Goudreau E, Minisi AJ, Davis AB, Mohanty PK.— Evidence against reinnervation of cardiac vagal afferents after human orthotopic cardiac transplantation. Circulation Aug. 1, 1995; 92(3):402-8; 17.

Arrowood JA, Minisi AJ, Goudreau E, Davis AB, King AL. Absence of parasympathetic control of heart rate after human orthotopic cardiac transplantation. Circulation. Nov. 18, 1997; 96(10):3492-8; 18.

Raczak G, La Rovere MT, Mmtara A, Assandti J, Prpa A, Pinna GD, Maestri R, D'Armini AM,Vigano M, Cobelli F. Arterial baroreflex modulation of heart rate in patients early after heart transplantation: lack of parasympathetic reinnervation. J Heatt Lung Transplant. May 1999; 18(5):399-406.

Burke MN, McGim1 AL, Romans DC, Christensen BV, Kubo SH, Wilson RF. Evidence for functional sympathetic reinnervation of left ventricle and coronay arteries after orthotopic cardiac transplantation in humans. Circulation. Jan. 1, 1995; 91(1):72-8.

Ludwig J, Friedgen B, Herrmann G, Zahorsky R, Inselmann G, Simon R, Graefe KH, Nellessen U. Evidence for partial sympathetic cardiac reinnervation following cardiac transplantation. Eur J Cardiothorac Surg. 1994; 8(7):388-90.

Kaye DM, Esler M, Kingwell B, McPherson G, Esmore D, Jennings G. Functional and neurochemical evidence for partial cardiac sympathetic reinnervation after cardiac transplantation in humans. Circulation. Sep. 1993; 88(3): 1110-8.

Leger J, Croll RP, Smith FM. Regional distribution and extrinsic innervation of intrinsic cardiac neurons in the guinea pig. J Comp Nemol. May 10, 1999; 407(3):303-17.

Sutton R, Petersen ME. The clinical spectrum neurocardiogenic syncope. J Cardiovasc Electrophysiol. Jul. 1995;6(7):569-76.

Hocini M, Sanders P, Deisenhofer I, Jais P, Hsu LF, Scavee C, Weerasmiya R, Raybaud F, Macle L, Shah DC, Garrigue S, Le Metayer P, Clementy J, Haissaguerre M. Reverse remodeling of sinus node function after catheter ablation of atrial fibrillation in patients with prolonged sinus pauses. Circulation. Sep. 9, 2003; 108(10):1172-5. Epub Sep. 2, 2003.

Haissaguerre M, Jais P, Shah DC, Takahashi A, Hocini M, Quiniou G, et al. Spontaneous initiation of atrial fibrillation by ectopic beats originating in the pulmonary veins. N Engl J Med 1998; 339: 659-666. (AF).

Haissaguerre M, Jais P, Shah DC, Garrigue S, Takahashi A, Lavergne T, et al. Electrophysiological End Point for Catheter Ablation of Atrial Fibrillation Initiated From Multiple Pulmonary Venous Foci— Circulation. 2000; 101:1409-1417.

Jais P, Haissaguerre M, Shah DC, et al. A focal source of atrial fibrillation treated by discrete radiofrequency ablation. Circulation 1997; 95:572-6.

Seshadri N, Marrouche NF, Wilber D, Packer D, Natale A.—Pulmonary vein isolation for treatment of atrial fibrillation: recent updates. Pacing Clin Electrophysiol. Jul. 2003; 26(7 Pt 2):1636-40.

Sanders P, Morton JB, Deen VR, Davidson NC, Sparks PB, Vohra JK, Kalman JM.—Immediate and long-term results of radiofrequency ablation of pulmonary vein ectopy for cure of paroxysmal atrial fibrillation using a focal approach. Intern Med J. May-Jun. 2002; 32(5-6):202-7.

Tada H, Oral H, Wasmer K, Greenstein R, Pelosi F Jr, Knight BP, et al. Pulmonary vein isolation: Comparison of bipolar and unipolar electrograms at successful and unsuccessful ostial ablation sites. J Cardiovasc Electrophysiol 2002; 13: 13.

Rocha Neto AC, Farias RL, de Paola AA. Treatment of atrial fibrillation with radio frequency ablation and simultaneous multipolar mapping of the pulmonary veins. Arq Bras Cardiol. Nov. 2001; 77(5):407-28.

Pappone C, Rosanio S, Oreto G, Tocchi M, Gugliotta F, Vicedomini G, Salvati A, Dicandia C, Mazzone P, Santinelli V, Gulletta S, Chierchia S. Circumferential radiofrequency ablation of pulmonary vein ostia: A new anatomic approach for curing atrial fibrillation. Circulation. Nov. 21, 2000; 102(21):2619-28.

Macle L, Jais P, Scavee C, Weerasooriya R, Hocini M, Shah DC, Raybaud F, Choi KJ, Clementy J, Haissaguerre M.—Pulmonary vein disconnection using the LocaLisa three-dimensional nonfluoroscopic catheter imaging system—J Cardiovasc Electrophysiol. Jul. 2003; 14(7):693-7.

Pappone C, Rosanio S, Augello G, Gallus G, Vicedomini G, Mazzone P, Gulletta S, Gugliotta F, Pappone A, Santinelli V, Tortoriello V, Sala S, Zangrillo A, Crescenzi G, Benussi S, Alfieri 0. Mortality, morbidity, and quality of life after circumferential pulmonary vein ablation for atrial fibrillation: outcomes a controlled nonrandomized long-term study. J Am Coll Cardiol. Jul. 16, 2003; 42(2): 185-97.

Pappone C.—Atrial fibrillation—a curable condition? Eur Heart J. Apr. 2002; 23(7):514-17.

Marchlinski FE, Callans D, Dixit S, Gerstenfeld EP, Rho R, Ren JF, Zado E.—Efficacy and safety of targeted focal ablation versus PV isolation assisted by magnetic electroanatomic mapping. J Cardiovasc Electrophysiol. Apr. 2003; 14 (4):358-65.

Morady, F.—Treatment of Paroxysmal Atrial Fibrillation by Pulmonary Vein Isolation. Circ J 2003; 67: 567-571.

Chen SA, Hsieh MH, Tai CT, Tsai CF, Prakash VS, Yu WC, et al. Initiation of atrial fibrillation by ectopic beats originating from the pulmonary veins: Electrophysiological characteristics, pharmacological responses, and effects of radiofrequency ablation. Circulation1999; 100: 1879-1886.

Natale A.—Radiofrequency ablation of the pulmonary veins: can it stop atrial fibrillation at its source? Cleve Clin J Med. Jan. 2001; 68(1):17, 21-2, 24.

Horlitz M, Schley P, Shin Di, Muller M, Sause A, Krolls W, Marx R, Klein M, Bufe A, Lapp H, Gulker H. Catheter ablation of ectopic atrial tachycardia by electrical pulmonary vein Disconnection. Z Kardiol. Feb. 2003; 92(2):193-9.

Chen YJ, Chen SA, Chang MS, Lin CI. Arrhythmogenic activity of cardiac muscle in pulmonary veins of the dog: Implication for the genesis of atrial fibrillation. Cardiovasc Res 2000; 48: 265-273; 43.

Asenjo R, Morris R, Oyarzum R, Dussaillant G, Ortiz M, Nicola M, Tapia E, Valencia M, Sandoval M, Morales P, Avalos V, Pezoa B, Von Krestschmann L, Abufhele A, Oyonarte M. Focal atrial fibrillation. Clinical characteristic and results of radiofrequency ablation. Rev Med Chil. May 2002; 130(5):482-94.

Jais P, Hocini M, Macle L, Choi Kj, Deisenhofer I, Weerasooriya R, Shah DC, Garrigue S, Raybaud F, Scavee C, Le Metayer P, Clementy J, Haissaguerre M. Distinctive electrophysiological properties of pulmonary veins in patients with atrial fibrillation. Circulation. Nov. 5, 2002; 106(19):2479-85.

Oral H, Knight BP, Ozaydin M, Chugh A, Lai SW, Scharf C, Hassan S, Greenstein R, Han JD, Pelosi F Jr, Strickberger SA, Morady F. Segmental ostial ablation to isolate the pulmonary veins during atrial fibrillation: feasibility and mechanistic insights. Circulation. Sep. 3, 2002; 106(10):1256-62.

Cox JL, Ad N, Palazzo T, Fitzpatrick S, Suyderhoud JP, DeGroot KW, Pirovic EA, Lou HC, Duvall WZ, Kim YD.—The Maze-III procedure combined with valve surgery. Semin Thorac Cardiovasc Surg. Jan. 2000; 12(1):53-5.

Sueda T, Nagata H, Orihashi K, Morita S, Okada K, Sueshiro M, Hirai S, Matsuura Y. Efficacy of a simple left atrial procedure for chronic atrial fibrillation in mitral valve operations. Ann Thorac Surg. Apr. 1997; 63(4): 1070-5.

Jatene MB, Marcial MB, Tarasoutchi F, Cardoso RA, Pomerantzeff P, Jatene AD. Influence of the maze procedure on the treatment of rheumatic atrial fibrillation—evaluation of rhythm control and clinical outcome in a comparative study. Eur J Cardiothorac Surg. Feb. 2000; 17(2): 117-24.

Adragao P, Cavaco D, Aguiar C, Palos J, Morgado F, Ribeiras R, Abecasis M, Neves J, Bonhorst D, Seabra-Gomes R. Ablation of pulmonary vein foci for the treatment of atrial fibrillation; percutaneous electroanatomical guided approach. Europace. Oct. 2002; 4(4):391-9.

Deneke, T., Khargi, K., Grewe, P.H., Laczkovics, A., von Dryander, S., Lawo, T., Muller, K.-M., Lemke, B. Efficacy of an additional MAZE procedure using cooled-tip radiofrequency ablation in patients with chronic atrial fibrillation and mitral valve disease, European Heart Journal, Journal of the European Society of Cardiology, Apr. 2002, vol. 23, No. 7, 558-566.

Pachon M* Jose C., Pachon M, Enrique I., Pachon M, Juan C., Lobo, Tasso J., Pachon, Maria Z., Vargas, Remy N.A., Pachon, Denilda Q.V., Lopez M, Francisco J., Jatene, Adib D. A new treatment for atrial fibrillation based on spectral analysis to guide the catheter RF-ablation, The European Society of Cardiology, Aug. 2004, 590-601.

APPARATUS AND METHODS FOR ARRHYTHMIA TREATMENT BASED ON SPECTRAL MAPPING DURING SINUS RHYTHM

CROSS-REFERENCE TO RELATED APPLICATIONS

This application is a continuation of U.S. application Ser. No. 11/202,049 filed 11 Aug. 2005 now U.S. Pat. No. 7,819,862 captioned, "Method of Arrhythmias Treatment Based on Spectral Mapping during Sinus Rhythm" (the '862 patent) the entire contents of the '862 patent are hereby incorporated by reference as though fully set forth herein.

BACKGROUND OF THE INVENTION a. Field of the Invention

The present invention relates to an ablation method and apparatus, e.g., such as those used for cardiac therapy. More particularly, the present invention pertains to methods that use spectral endocardial analysis for treatment of bradycardias and atrial fibrillation to control and/or provide information regarding ablation processes.

b. Background Art

Catheters for electromagnetic ablation are known and are commonly used to treat various diseases and medical disorders. Typically, the catheter includes an energy-delivering electrode that is coupled to a source of electromagnetic energy, e.g., an electrosurgical generator. Other electrodes can be proximally positioned on the catheter and can be used for sensing and other related electrical purposes.

Also known are steerable catheters. Such catheters include a handle and a deflection mechanism that is operable to effect deflection of the distal end of the catheter in order to facilitate navigation of the catheter through the tortuous pathways of a patient's vasculature.

In prior procedures, an ablation catheter is employed to alter tissue. In order to ablate the tissue, electromagnetic energy is applied to create a lesion via the energy-delivering electrode without regard to the specific level of electromagnetic energy supplied by the generator. In situations where too much electromagnetic energy is delivered to the tissue during the electrosurgical procedure, the tissue "pops", thus indicating the application of an excessive amount of energy.

Several clinical conditions comprise transitory or permanent autonomic dysfunction by increasing the vagal action and sympathetic driving reduction. As a consequence, transitory or permanent, symptomatic or asymptomatic sinus bradycardias or pauses or transitory AV block may occur. The most typical examples are the cardio inhibitory or mixed neurocardiogenic syncope, carotid sinus syndrome and the functional transitory AV block.

Despite having apparently normal hearts theses patients may be very symptomatic and refractory to conventional medication. Consequently they represent a difficult problem for the cardiologist as far as many of them are referred to the permanent pacemaker implantation. Furthermore we have to add to this group a considerable number of patients presenting a significant sinus and AV node dysfunction with good atropine response suggesting that an important portion of the vagal innervations is still preserved.

A pacemaker has been used, as the last option, to treat the malignant neurocardiogenic syncope. Its indication is uncomfortable in a young and apparently normal heart patient. Furthermore, recent studies have shown the cardiac stimulation has not been a good solution for all the cases of neurocardiogenic syncope. Several studies have shown that a great number of parasympathetic efferent fibers and autonomic ganglia surround the sinus and AV nodes regions.

BRIEF SUMMARY OF THE INVENTION

We hypothesized that a large amount of the efferent parasympathetic innervations might be eliminated by endocardial catheter radiofrequency ("RF") ablation in these areas allowing the cure or the clinical control of these conditions. In this case the main challenge would be to develop a safe method to locate the vagal fibers entrance to the atrial wall.

The present invention describes methods to identify the atrial wall points having high density autonomic innervation.

The present invention also refers to show that the RF ablation of these regions may result enough parasympathetic denervation to be used for the clinical control of the neurocardiogenic syncope, functional AV blocks, sinus node dysfunction and the carotid sinus syndrome.

The functional bradycardia arrhythmias considered in this study comprise persistent or permanent sinus bradycardia or AV block in the absence of evident cardiopathy being corrected by atropine. It is known that clinically they are present as the sinus bradycardia, AV blocks, cardio inhibitory or mixed neurocardiogenic syndrome and in the carotid sinus syndrome being mediated essentially by increase of the efferent parasympathetic effect. Reduction of the sympathetic tonus may also exist. In basal conditions there is a permanent and important parasympathetic effect which upon withdrawal of said effect causes significant heart rate augmentation as may be seen during the atropine test.

It is known that the Fourier Transform is a mathematical tool that allows the visualization of the frequency spectrum (the frequencies of sinus waveforms whose sum makes the original wave) of any wave (frequency domain). Nowadays, there is a simplified method to carry out the Fourier Transform named "Fast Fourier Transform" or FFT. Joseph Fourier was a French mathematician who discovered that practically any wave could be represented as a sum of sinus waves (frequency spectrum). In general, in electrophysiology the waves are displayed on a time basis (time domain).

Therefore, it can be said that while the EKG enables us "to see", the FFT enables us "to hear" the P-QRS complexes. By applying the FFT to the endocardial signals we can study frequencies of up to 500 Hz depending on the filters applied during the recordings. As a rule, in the myocardium, the more organized the conduction, the narrower the frequency spectrum of the signal, FIG. 13-2A.

Cardiac Autonomic Nervous System Parasympathetic

Seeking the AF Substratum: Aiming at studying the atrial myocardium electrical features, we have used the spectral analysis through the fast Fourier transform (FFT), thus obtaining beyond the time domain, the frequency domain of the atrial potentials. For this purpose, we have developed a software program that works with a 32 channel-polygraph, permitting us to obtain the FFT of the endocardial signals. By using this tool, we have found two types of atrial myocardium: the first one, that we have named as "compact", works like one isolated cell—the classical well known myocardial behavior. Compact presents homogeneous, fast conduction with all cells working in-phase and normal refractory period.

The FFT of these tissue potentials presents a well-defined shape with one high power fundamental frequency and fast uniformly decreasing harmonics. In the FIG. 13-2A it may be observed that most frequencies are left sided. On the other hand, the second type of myocardium that we have named as "fibrillar" is similar to a bunch of nervous cells. Fibrillar is characterized by relatively independent fascicles with heterogeneous and out-of-phase conduction. Fibrillar has a short refractory period allowing for a faster activation rate than the surrounding myocardium. The FFT of these tissue potentials show a low power, fragmented, and heterogeneous profile suggesting it to be a bundle of distinct cell bunches. Besides its fundamental frequency, the fibrillar FFT has a greater number of irregular harmonics of high amplitude and marked leaps. The relative high amplitude of these signals with high frequency causes a "right-shifting" of the FFT, FIG. 13-2B.

The pre-ganglionic fibers are located in the central nervous system more specifically in the oblongate medullae at the vagus nerve dorsal nucleus. By the vagi nerves they continuously pass until the cardiac wall where they connect with the postganglionic cells whose fibers are very short having not more than several millimeters because their body cells are located in the atrial wall or in the para-cardiac ganglia.

The atria receive much more cholinergic innervation than the ventricles thus having higher amounts of acethilcholine, cholina-acethil-transferase and acetil-cholinesterase. The cardiac parasympathetic effect is an important reduction of the automatism, excitability and conductibility. The contractility is less reduced because of the small number of parasympathetic vagal fibers in ventricles. (FIG. 1).

Parasympathetic Ganglia

A great amount of post-ganglionic parasympathetic body cells are located outside the atrial wall in the ganglia related to the atria or great vases. Animal studies have shown 3 main parasympathetic ganglia located in para-cardiac fat-pads:

1. Ganglion A, located between the superior vena cava and the aortic root just above the right superior pulmonary vein;

2. Ganglion B, located between the right superior pulmonary vein and the right atrium; and 3. Ganglion C, located between the inferior vena cava and the right/left atrium.

The ganglion B originates most of the cardiac parasympathetic innervation. The ganglion C gives origin to the main part of the AV node innervation. Most of the vagal efferent cardiac fibers pass through the ganglion A and onto the ganglia B and C. Only a few efferent fibers enter the B and C ganglia directly. Therefore, it is feasible to get a parasympathetic denervation by ablating the ganglion B, and AV nodal denervation by ablating the ganglia C. However, ablation of the A ganglion provides a significant sinus and AV node denervation. (FIG. 2).

The efferent sympathetic cardiac nervous system comprises at least two long fibers traveling away from the spinal cord to the heart. The preganglionic body cell is located at the spinal cord intermedio-lateral horn. Its axon reaches the spinal nervous by the anterior root and the para-vertebral ganglion by the white branch. The para-vertebral sympathetic chain contains the postganglionic sympathetic neuron body cell. Their axons travel through the cardiac nerves (4 or 5 slender branches on each side) which emerge from the 3 inferior cervical and from the 4 superior thoracic sympathetic ganglia. The fusion of the cervical inferior and thoracic superior ganglia forms the "stellate ganglion". The noradrenalin released from the sympathetic postganglionic fibers increases all the cardiac properties: automatism, excitability, conduction and contractility.

Alternative, less invasive approaches have recently been adopted for treatment of cardiac arrhythmias in a clinical setting. The present invention considers the body cells of the postganglionic parasympathetic fibers to be located in the atrial wall or in the para-cardiac ganglia. We hypothesized that would be possible to treat functional bradycardias by endocardial catheter RF-ablation. It could provide some amount of permanent parasympathetic denervation by eliminating the postganglionic parasympathetic cells. The main challenge would be to map these fibers on the endocardial wall. Therefore we had to develop a method to detect the endocardial point of high innervation density.

By studying the spectrum of the endocardial potentials by the Fast-Fourier-Transformation (FFT) we have found two kinds of atrial myocardium: the compact and the fibrillar. The former presents a homogeneous spectrum with one main frequency around 50 Hz and uniform conduction resulting from a mass of very well connected cells. The latter presents a heterogeneous and coarse segmented spectrum with several segments presenting frequencies higher than 100 Hz shifting its FFT to the right, FIG. 4. The latter appears to be composed of cell bundles working as a bunch of filaments. (FIG. 3).

The parasympathetic fibers entrance occurs mainly in the atrial wall. The presence of the nervous fibers mixed with myocardial cells changes the myocardial conduction from the compact to the fibrillar pattern, FIG. 3. In absence of cardiopathy we have found the fibrillar spectrum mainly in the sinus and in the AV node area but it may also be found in several other places mostly in the regions near the three para-cardiac ganglia, FIG. 2.

In this invention the fibrillar pattern of conduction was used as a marker of the nervous-myocardium interface. The present invention has certain objectives: The aim of this study has been to use the RF-ablation to eliminate some amount of cardiac parasympathetic innervation in order to change the autonomic drive thus enabling the cure of the neurocardiogenic syndrome, of the functional AV blocks and of the sinus node dysfunction without pacemaker implantation.

DETAILED DESCRIPTION OF THE INVENTION

Figure 1:
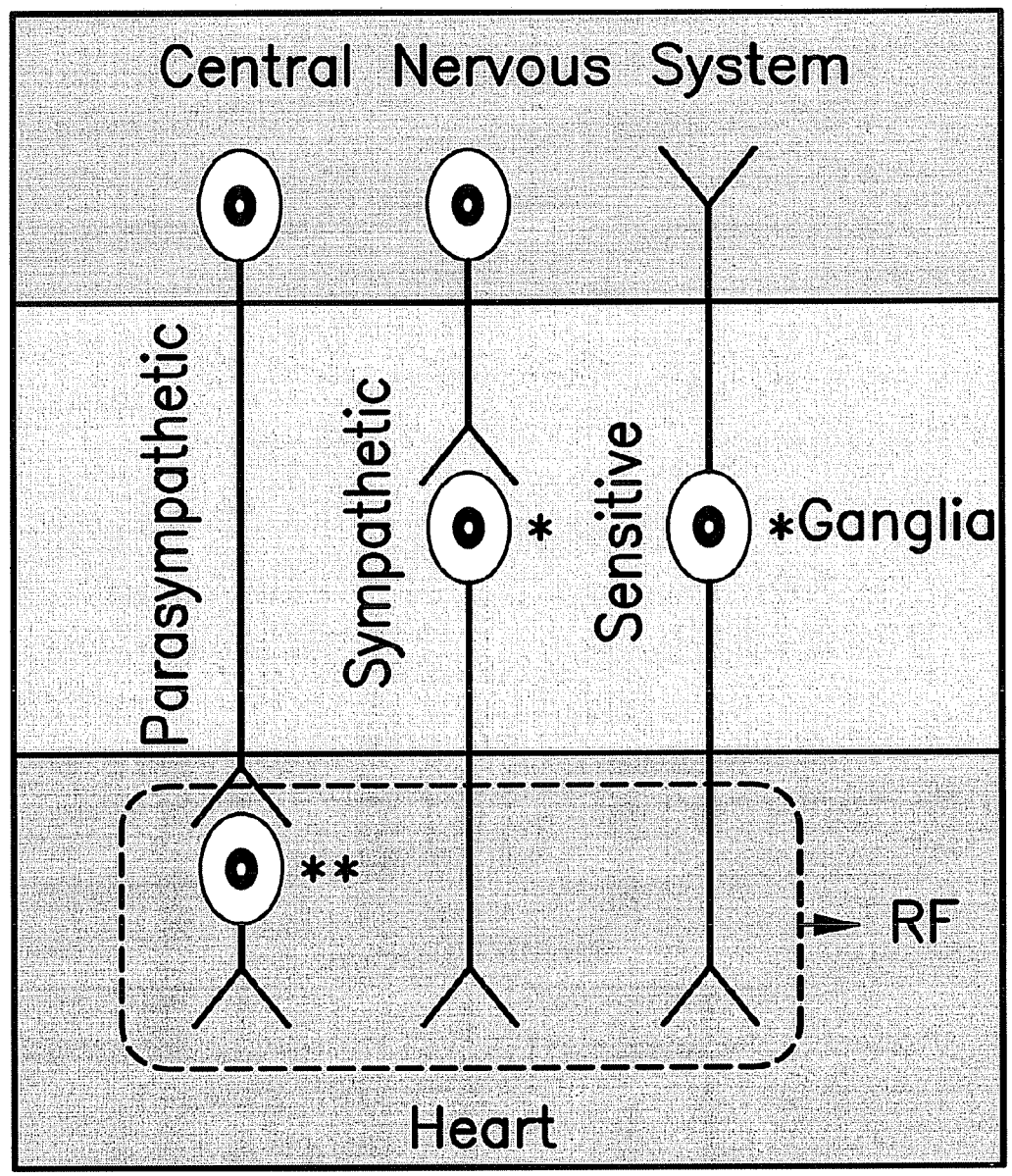
FIG. 1 is a schematic diagram of the cardiac innervation. The postganglionic sympathetic and sensitive body cells (denoted by an asterisk "*" in FIG. 1) are located in ganglia far from the heart. The body cell of the postganglionic parasympathetic neuron is located in the atrial wall or in the para-cardiac ganglia. The rectangle depicted in ghost in FIG. 1 and denoted by the arrow toward the letters "RF" are structures affected by catheter RF ablation in the atrial wall. The parasympathetic innervation (denoted by double asterisks "**" in FIG. 1) is the most affected one due to the postganglionic neuron body cell elimination.

The study population consisted of 21 patients (pts.) [4F, 17M] with mean ages of 47.5±16 ranging from 19 to 70 years old, presenting symptomatic functional bradyarrhythmias (palpitations 10 pts., dizziness 16 pts. and syncope 7 pts.). There was no significant structural cardiopathy (EF=0.63±0.4). The diagnoses were neurocardiogenic syncope 6 pts., intermittent high degree AV block 7 pts. (3 of them occurring only while sleeping) and sinus dysfunction 13 pts. (being associated with brady-tachycardia syndrome in 9 pts.). All the patients were exhaustively studied by Holter, tilt-test, stress-test, conventional EP study and by atropine test having well established the functional bradyarrhythmia diagnosis.

After having written consent of the patients, the procedures were performed with general endovenous anaesthesia controlled with system Dratger Cicero E M. The vital signs (heart rate, oximetry, blood pressure, pletismography, peripheral perfusion, capinography and respiratory gases) were monitored by Merlin Agilent/Philips polygraph. The brain functions were directly controlled by the system BIS Aspect A-1000 keeping the conscious level between 40 and 50 bispectral index. The cerebral oximetry was measured by frontal infra-red spectroscopy (NIRS-Cerebral Oxymeter Somanetics-INVOS) keeping the $sRO_2 \geq 75\%$ of the pre-induction levels. After having reached the anesthetic level (BIS index between 40 and 50) the procedure was performed with one transesophageal echocardiogram to discard intra-cardiac thrombus and for guiding a transseptal puncture.

The conventional EP leads were placed and a routine EP study was carried out. Heparin (5,000 to 10,000 IU) was used to maintain the activated coagulation time around 250 s. All the patients were treated in sinus rhythm undergoing spectral and anatomical guided ablations using a 4 mm catheter (EPT-Blazer) with the thermo-controlled system Biotronik MDS.

Spectral Guided Ablation

Spectral mappings were obtained in a conventional 32 channel EP polygraph (TEB-32), with specific customized software for spectral analysis (Pachon-TEB2002). A special pre-amplifier was assembled to get the on-line spectral analysis using the software Sigview 1.9. Simplified spectral analysis was obtained by means of specific 3 band-passes filters by using the conventional polygraph (30-500 Hz, 100-500 Hz and 300-500 Hz).

Figure 4:
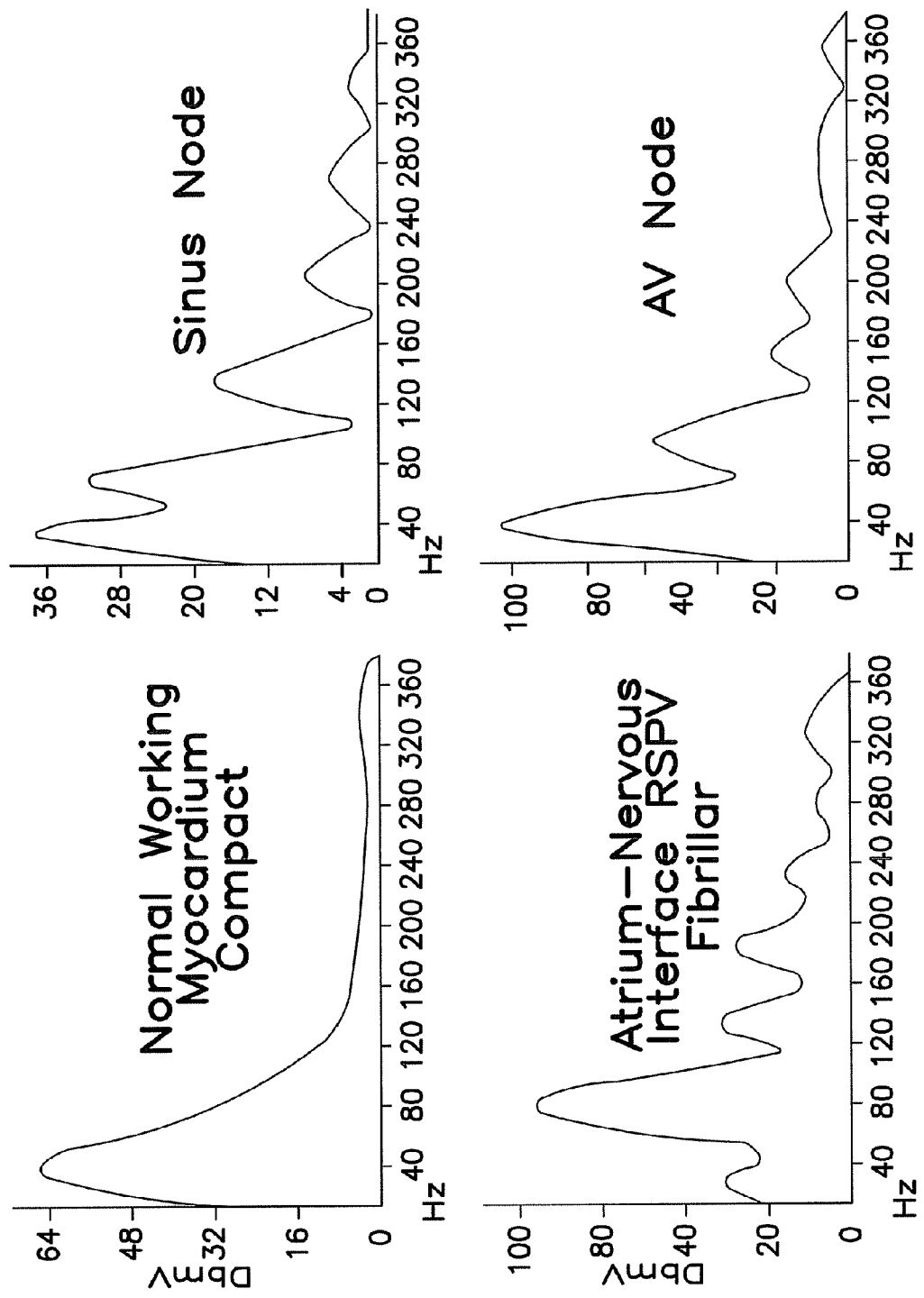
FIG. 4 shows spectra obtained from 4 endocardial places in the left and right atria. The working myocardium (compact) registered in this case in the LA roof presents a homogeneous spectrum with main frequencies at 40 Hz in this example. All the other examples are showing fibrillar pattern with very segmented spectra and important frequencies shifted to the right like the atrium-nervous interface observed near the insertion of the right superior pulmonary vein (RSPV). This is the typical spectrum we have sought for cardioneuroablation. It is important to remark that the sinus and AV node regions present a typical fibrillar pattern. Probably the fibrillar pattern occurs there because of the very close relation of these structures with the nervous system.

In this way, studying the potentials over 100 Hz and 300 Hz, an excellent correlation with the on line spectral analysis was achieved allowing the procedure to be carried out also without on-line spectral analysis, FIG. 4. Thermo controlled RF limited at 30 Joules ("J") was applied in all the points having segmented and right-shifted spectrum. Near the pulmonary veins 60° C./15 s was used. Other points were treated with 70° C./30 s or until having eliminated the fractionated potentials above 300 Hz.

Anatomical Guided Ablation

Figure 5:
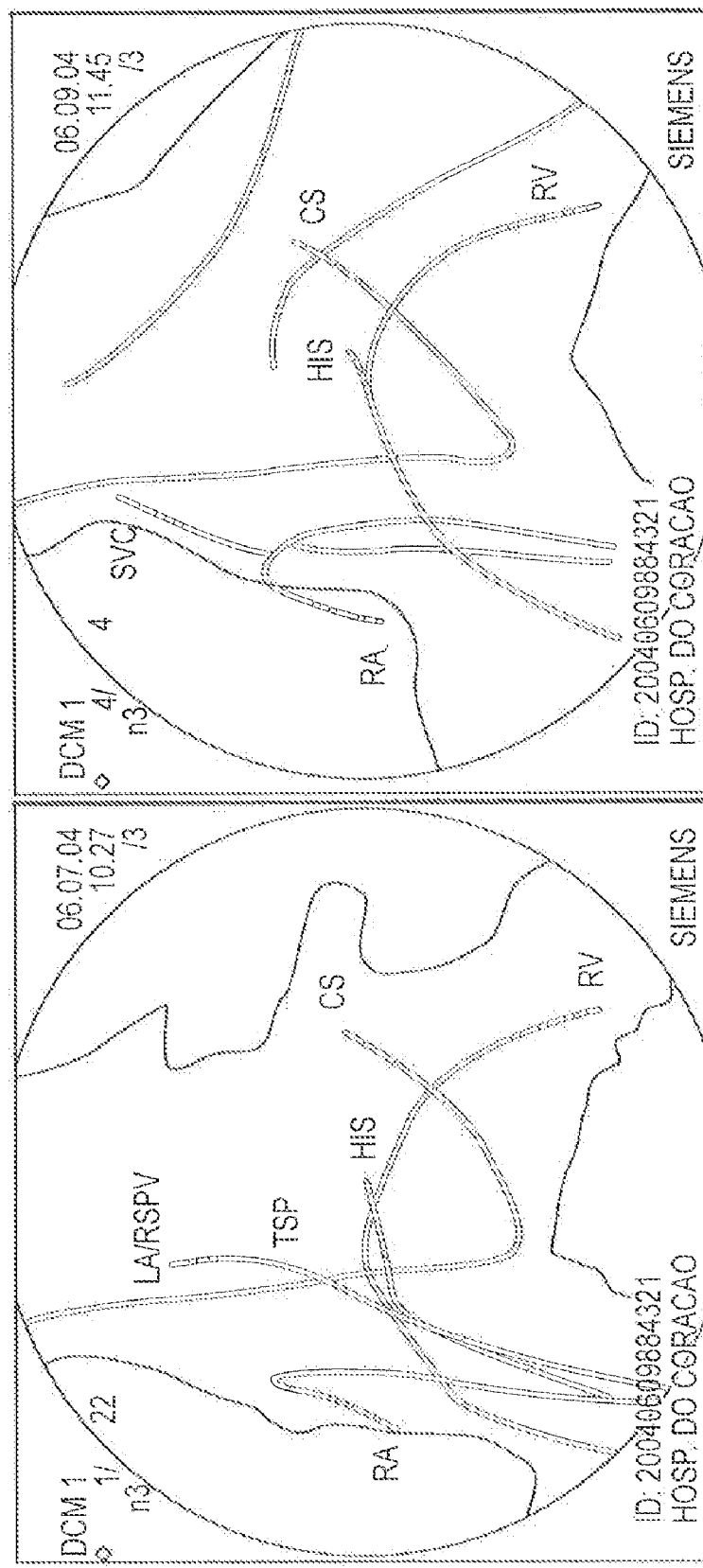
FIG. 5 shows a methodology for anatomical ablation. The first para-cardiac ganglion is ablated near the superior vena cava medial wall (denoted by two asterisks "**" in FIG. 1). The approach for the second ganglion is the left atrium endocardium close to the insertion of both right pulmonary veins (denoted by an asterisk "*" in FIG. 1) and the C ganglion is treated by the medial wall of the inferior vena cava just below the atrium and in the ostium of the coronary sinus.

Having ablated all the regions presenting segmented right-shift spectra, endocardial anatomical ablation was also performed in the regions of the 3 epicardial fat-pads, one located between the aorta and the superior vena cava (treated through the superior vena cava), the second between the right pulmonary veins and the right atrium (treated through the left atrium) and the last in the right posterior interatrial septum near the inferior vena cava (treated through the inferior vena cava and through the coronary sinus). In these regions thermo-controlled RF was delivered for at least one minute at 70° C. with 30 J of maximal energy. (FIG. 5).

Immediate Endpoints of the Procedure

The procedures were aimed at getting:
1. Elimination of the potentials with right spectral shifting in the right and left atria regions surrounding the sinus node;
2. Persistent increase of the sinus rate;
3. Persistent increase of the Wenckebach's point and
4. Anatomical ablation.

All the sinus and AV conduction electrophysiological parameters were measured and compared before and after the ablation. Oral anticoagulation with International Normalized Ratio or "INR" (for blood-clotting time) between 2 and 3 was maintained during 2 months after the procedure. All the patients having neurocardiogenic syncope were studied again with tilt-test at 1 and 6 months after the ablation. Holter testing was repeated at 1, 2, 6 months and at 1 year, and a stress-test was performed after 2 months of follow-up. The mean follow-up was of 9.2±4.1 months. Statistical analyses were obtained with mean value±SD and the Student t-Test for non-categorical variables. A p-value<0.05 was considered to be significant.

The purposes of the present invention procedures were accomplished using the described procedures in 20 of 21 patients. In one pt. having an anatomical anomaly the transseptal puncture was avoided due to high risk of bleeding. In two pts. sinus node denervation was tried without accessing the left atrium. In 3 pts. only the AV node denervation was planned to be accessed by the right atrium. In nine pts. having sinus bradycardia and episodes of paroxysmal atrial fibrillation (AF) a new technique of AF ablation was also performed based on the elimination of the "AF-Nests" in sinus rhythm.

Figure 6:
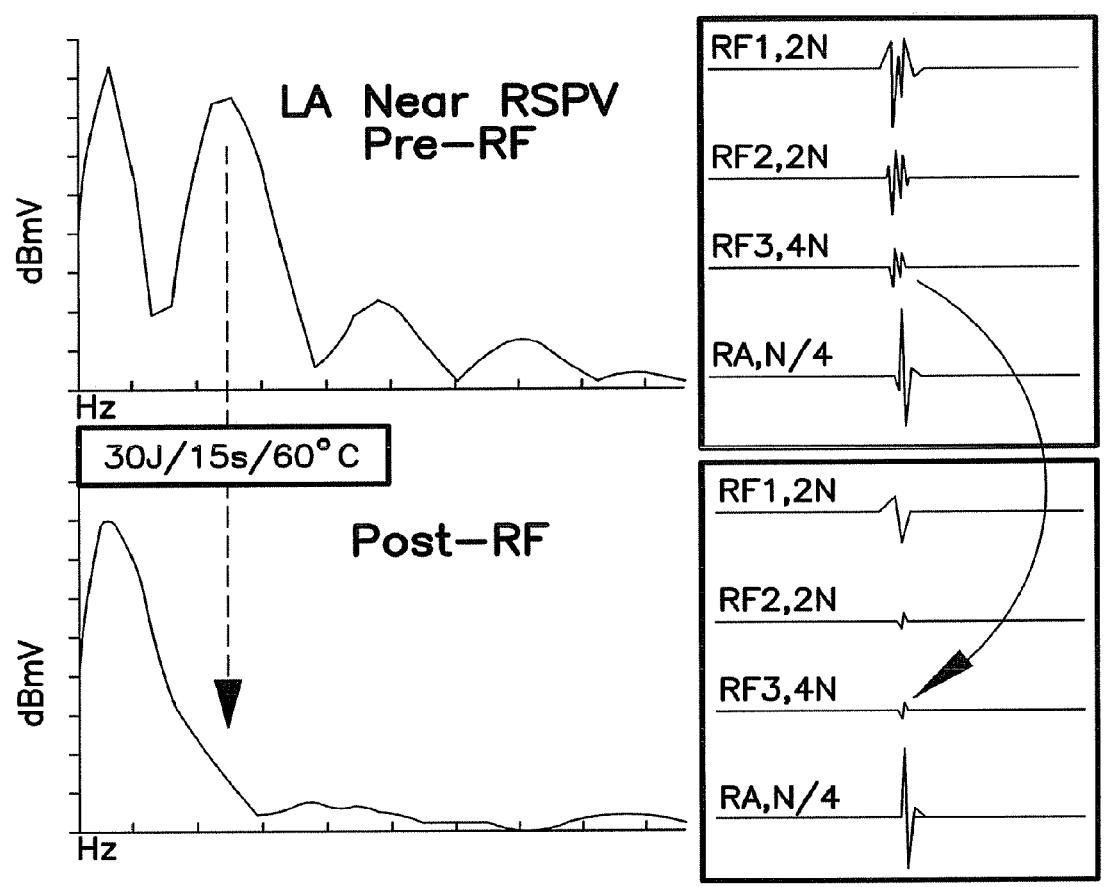
FIG. 6 is an example of the results of ablation in the left atrium near the right superior pulmonary vein (RSPV) insertion. On the left there is the spectrum pre (upper) and post-ablation (bottom). The former presents a segmented spectrum with right-shift frequencies (fibrillar pattern). After ablation the high frequencies are nearly eliminated but the low frequencies are less affected so the fibrillar myocardium spectrum virtually changes into the compact pattern. On the right the same phenomenon may be observed in the time domain. Filtering the endocardial signals in 3 channels (RF1=30-500 Hz, RF2=100-500 Hz and RF3=300-500 Hz) it is feasible to get a kind of spectral analysis. The fibrillar myocardium typically presents polyphasic signals mainly in the second and third channels.

This technique does not interfere in the cardioneuroablation because it is based on the right spectral shifting as well. In the left atrium the typical segmented right shift spectrum was found at the insertion of the right superior and inferior pulmonary veins, in the roof and in the interatrial septum. In the right atrium, fibrillar myocardium was observed in the superior and inferior vena cava insertion, in the low portions of the crista terminalis and surrounding the coronary sinus ostium. A mean of 28.7±15 endocardial points were treated per patient. The mean X-ray time was 38.9±15.4 minutes. There were no complications. (FIG. 6). Even a low energy ablation was able to nearly eliminate the potentials in the third channel.

The possibility to act specifically on the cardiac autonomic innervation by endocardial RF catheter ablation corresponds to a new treatment with potentiality to several applications.

The functional bradyarrhythmias constitute an initial approach and a promising relatively safe model that could show how much we can move forward. It is probable that other pathologies like Long QT syndrome, Brugada syndrome, ventricular arrhythmias with autonomic modulation besides the sleep apnea, and so on could be targeted by the spectral mapping and endocardial ablation in the future.

The natural model of the cardiac innervation is highly suitable to this approach. The parasympathetic postganglionic neuron body cell is very susceptible to endocardial RF because it is located at (FIG. 1) or very close to the cardiac wall in the para-cardiac ganglia, FIG. 2. The elimination of the body cell makes the parasympathetic reinnervation more unlikely even than in cardiac transplantation.

Figure 2:
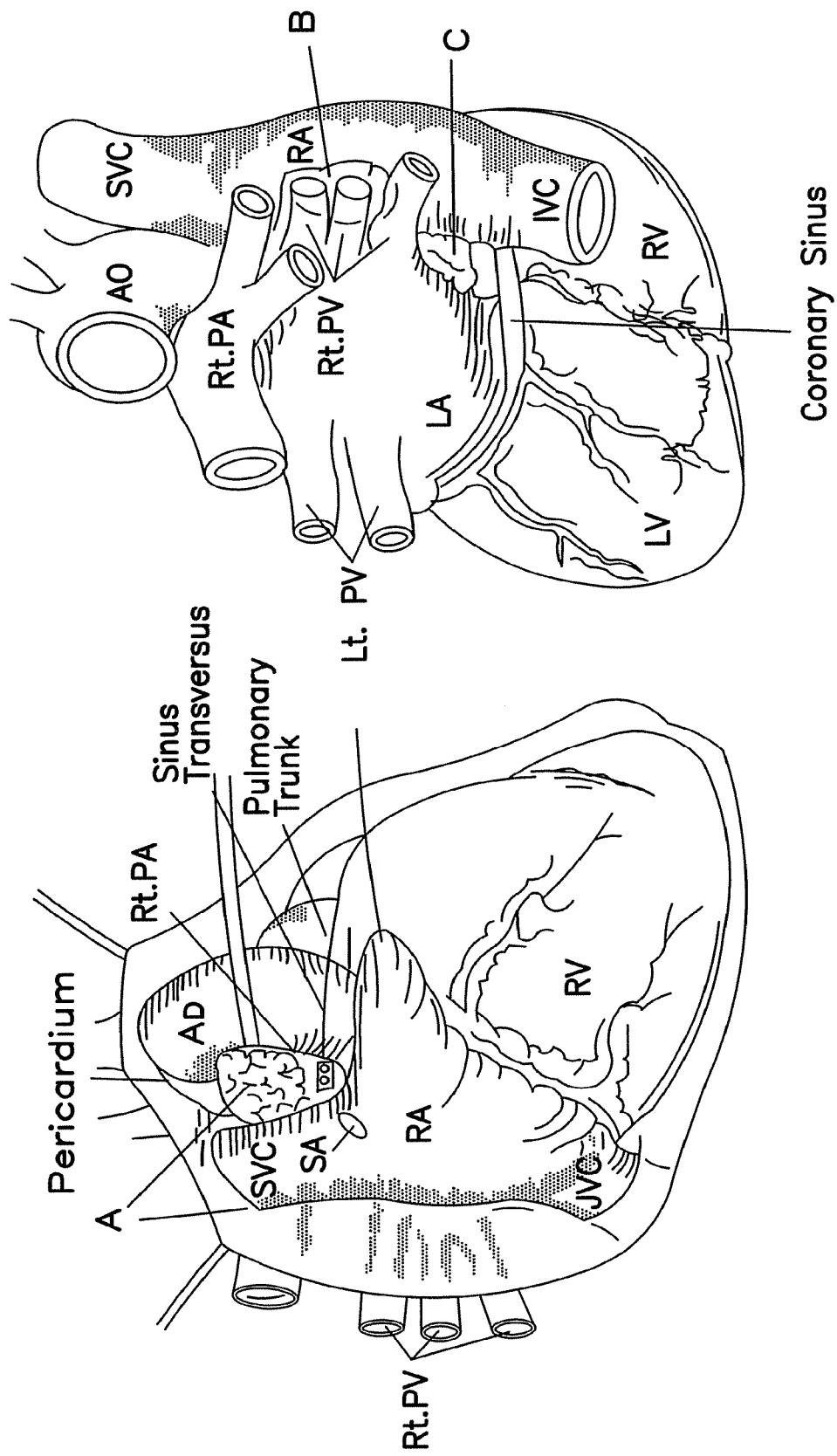
FIG. 2 is a pictorial diagram of the para-cardiac ganglia in the canine heart according to Zipes et al. 10. The first para-cardiac ganglion is located between the superior vena cava and the aorta (A); the second one is located between the right superior pulmonary vein and the right atrium (B) and the third one is located at the junction of the inferior vena cava, right atrium and left atrium (C).

On the other hand, the body cells of the sympathetic and the sensitive neurons remain far from the heart, FIG. 1. The RF ablation destroys only the fibers of these systems so they may present recovery. In this case, the reinnervation would be much more extensive and complete than that classically observed in the cardiac transplantation because the barriers created by the surgery are incomparably larger as the RF-ablation causes no anatomical disarrangement.

The fibrillar myocardium areas found in this study—right pulmonary vein insertion, LA roof, interatrial septum, near vena cava insertion, intercaval space and coronary sinus ostium, overlap with those of heart mammalian autonomic innervation described by Leger et al using immunoreactivity and fluorescence histochemistry techniques.

Figure 7:
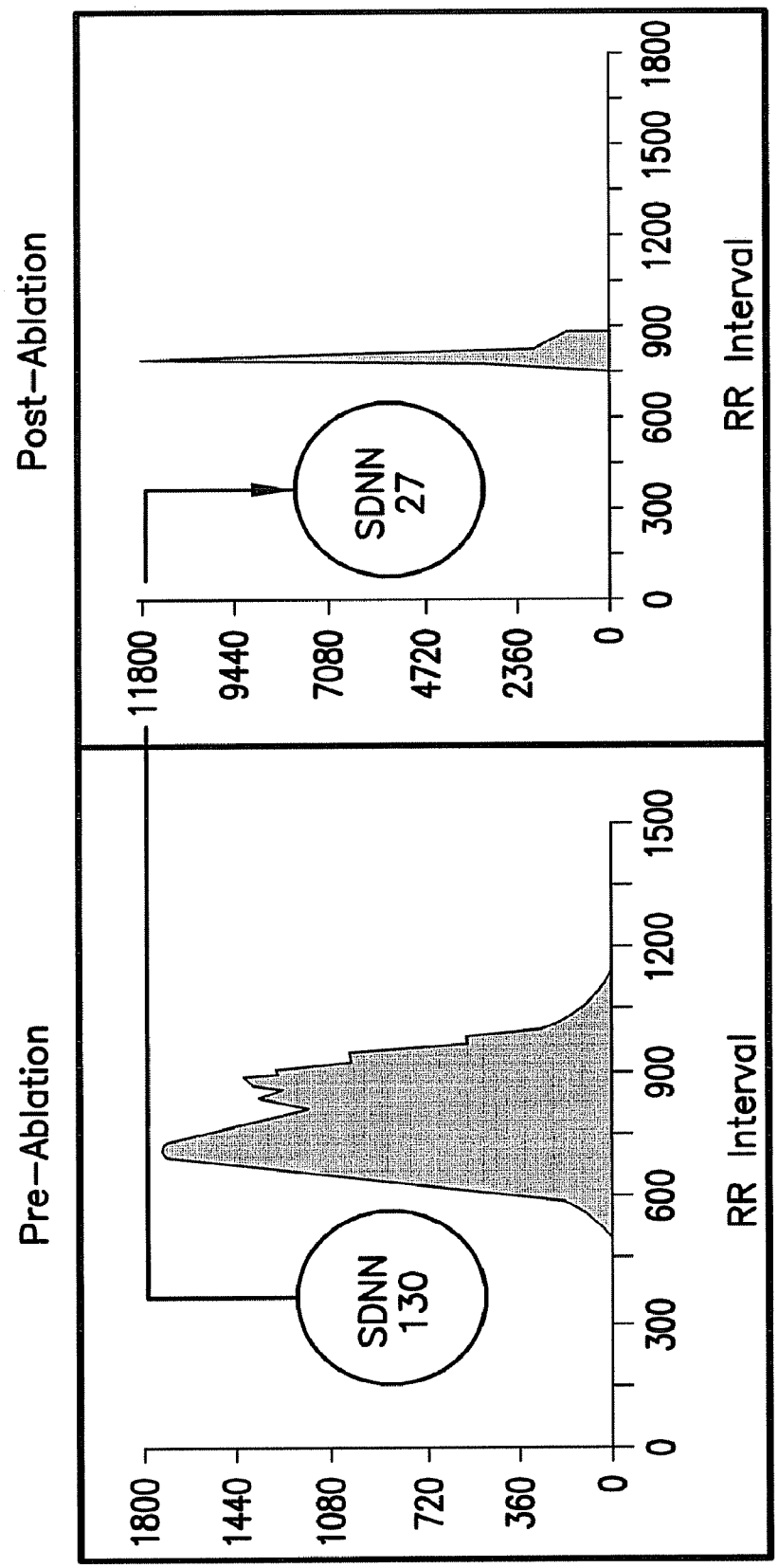
FIG. 7 shows the heart rate variability (HRV) pre- and two days post-cardioneuroablation of the sinus node autonomic nervous system. There is an important reduction of the HRV from SDNN=130 ms to 27 ms showing significant decreasing of the parasympathetic drive.

The acute autonomic denervation is very well proved by the intense reduction of the heart rate variability observed after the cardioneuroablation, FIG. 7 and Table 1. Nevertheless, in the chronic phase, a sympathetic reinnervation is observed that can be suspected by the recovery of the chronotropic response and by increase of the heart rate variability that remain in one intermediate level.

Figure 8:
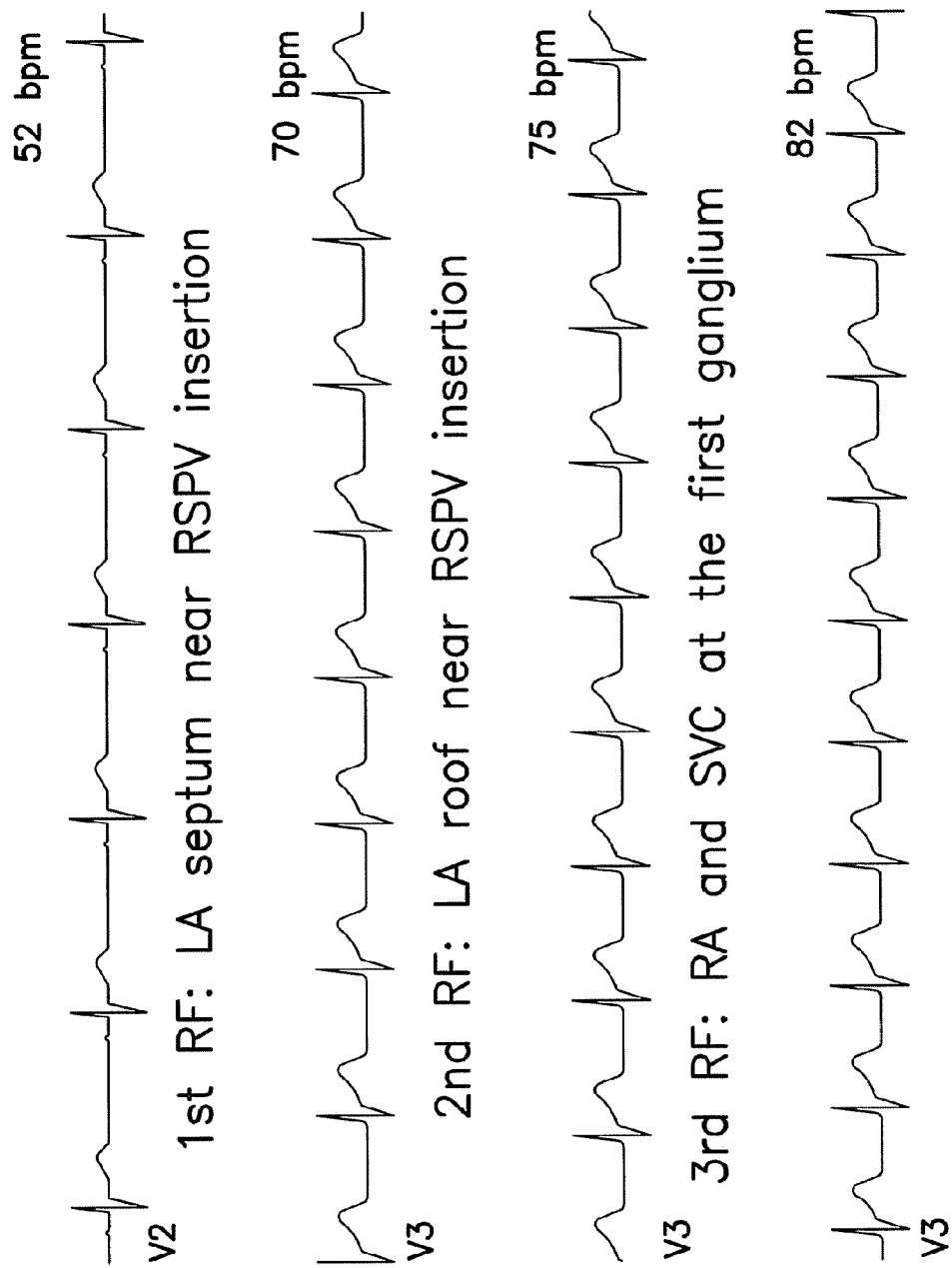
FIG. 8 shows a progressive increase of the heart rate caused by the ablation of the nervous autonomic input of the sinus node. The first two ablations were performed in the endocardium of the left atrium (LA) near the insertion of the right superior pulmonary vein (RSPV). The last one was performed in the right atrium in the lateral portion (crista terminalis) and in the medial wall of the superior vena cava targeting the ablation of the first epicardial fat pad (first ganglion).

Using this invention, it was feasible to get significant and persistent parasympathetic denervation with RF-ablation on the endocardial of the left and the right atria and in the cava veins. (FIG. 7) One interesting finding in this invention is that in the endocardium of the left and right atria there are points presenting typical, segmented and right-shifted spectrum that cause an immediate and persistent increase of the heart rate when ablated, FIG. 8. In general these points are located near the insertion of the right superior pulmonary vein and in the right atrium at the crista terminalis, being relatively different among the patients. In this study, the sinus rate increase ranged from 25% to 75% from the basal value. The endocardial potentials mapping and the spectrum of this area show this point to be composed of fibrillar myocardium, probably one of the most important interface being between the parasympathetic nervous system and the atrial myocardium, FIG. 6.

Neurocardiogenic Syncope

Neurocardiogenic Syncope can be malignant and refractory to medication resulting in serious reduction of the quality of life. Several different treatments have been proposed for this condition, but the outcome remains less than satisfactory. Despite the pacemaker having been the only option for severe cases, the second VPS II trial has shown it provides no significant protection.

Figure 9:
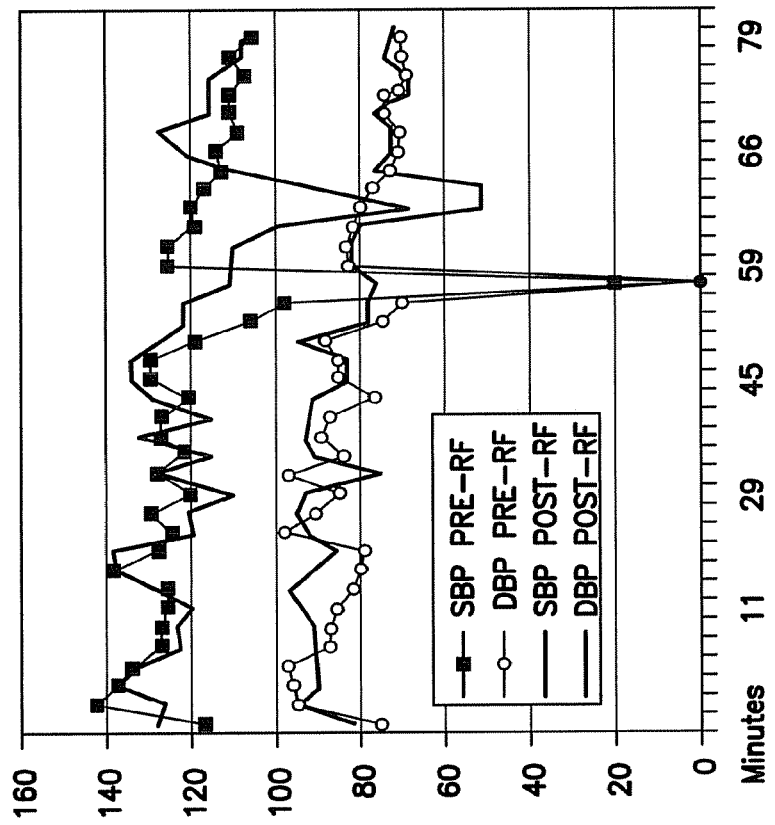
FIG. 9 shows that even in the neurocardiogenic syncope of the mixed type, the cardioneuroablation may be useful. In this case despite having not eliminated the vasodepressor response, the parasympathetic denervation prevented the heart rate drop. The patient that had been presenting asystole and syncope in the first tilt-test presented only dizziness in the control tilt-test. In this case, instead of heart rate falling or asystole it was remarked a heart rate increasing and the vasodepressor response attenuation thus avoiding the syncope.
Figure 9:
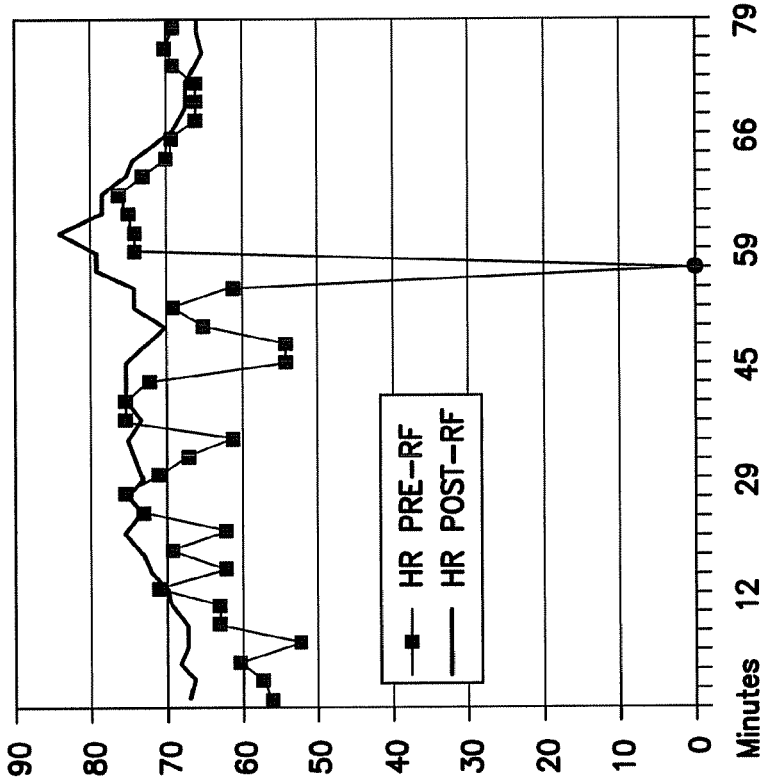

The neurocardiogenic syncope cases studied using the present invention were very serious. One of them presented asystole more than 20 seconds in the tilt-test. In this case the control tilt test after the ablation presented only a vasodepressor response without syncope keeping the heart rate near 85 bpm, (FIG. 9). Neither bradycardia nor asystole were observed. All the patients are evolving very well, without syncope or dizziness, but they are under close observation since it is a new treatment not well known by long term.

Furthermore, the denervation obtained by the cardioneuroablation has the specific aim to alter the cardiac autonomic nervous system only enough to get clinical control. Nevertheless the initial results and clinical outcome are highly promising. One of the possible limitations of this approach in the neurocardiogenic syncope is the specific and predominant effect on the efferent vagal fibers. Therefore it seems that only the cardio-inhibitory response would be treated, FIG. 9.

In other words, the vasodepressor type is not feasible for this treatment. However, eliminating the cardioinhibition of the mixed neurocardiogenic syncope may have a great and good influence in the outcome. (FIG. 9). Even in the case of neurocardiogenic syncope of the mixed type, cardioneuroablation may be useful. In this case despite having not eliminated the vasodepressor response, the parasympathetic denervation prevented the heart rate drop. The patient that had been presenting asystole and syncope in the first tilt-test presented only dizziness in the control tilt-test. In this case, instead of heart rate falling or asystole, the heart rate increased remarkably and the vasodepressor response attenuated thus avoiding the syncope.

Functional High Degree AV Block.

The patients of this group presented high degree AV block of functional origin. It appeared mainly while sleeping, ostensibly relieved of all significant physical stress and there was no evident cardiopathy. In spite of this, 4 pts. presented mild to moderate abnormalities of the AV conduction electrophysiological parameters (prolonged AH interval, reduced Wenckebach's point, prolonged AV refractory) which were normalized after ablation, FIG. 10.

In three patients, the procedure was accomplished only through right atrium. One of these patients despite having intermittent high degree AV block pre-ablation remains with nocturnal Mobitz I AV-block post-ablation. Although this result can be considered satisfactory, by studying other cases we have perceived better nodal AV denervation when the sinus node neural imputes are also treated. This fact may be explained because the most parasympathetic nodal AV fibers sprout from the cavo-aortic para-cardiac ganglion passing by the sinus region. Thus, we have also proceeded with the sinus node denervation in all the cases we have planned a more extensive AV nodal denervation, FIG. 10 and FIG. 11. Another example came from our initial experience with one patient presenting moderate sinus pauses and very long episodes of intermittent AV block (up to 6 seconds) for many years. He was treated only by the right atrium aiming at the AV node denervation. The AV block episodes were completely eliminated regardless the nocturnal moderate sinus pauses which remained unchanged. Obviously, in this case the denervation of the sinus node too would have been more suitable.

Figure 10:
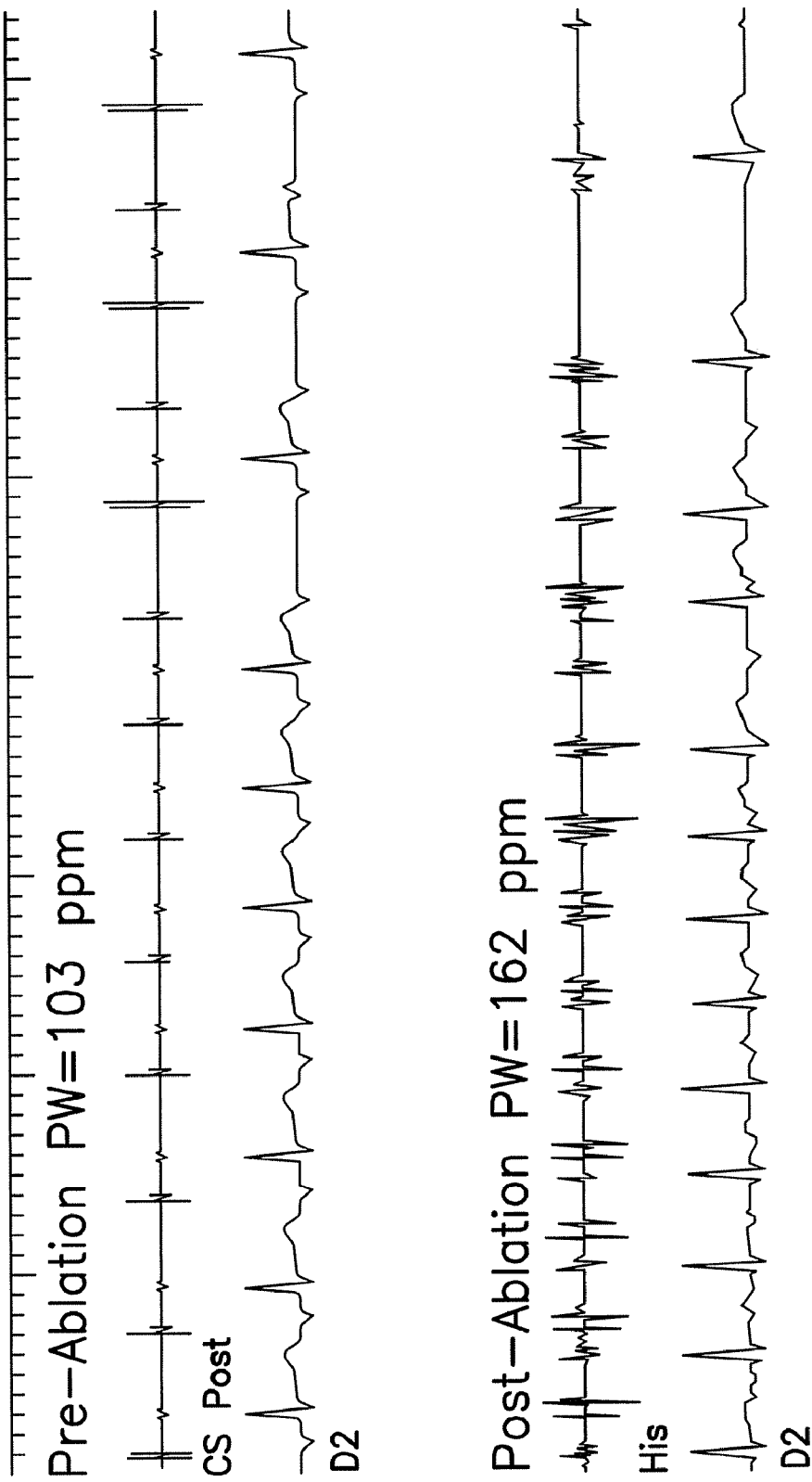
FIG. 10 shows a normalization of the Wenckebach point after the cardioneuroablation on the AV nodal region by spectral and anatomical mapping in the A ganglia.
Figure 11:
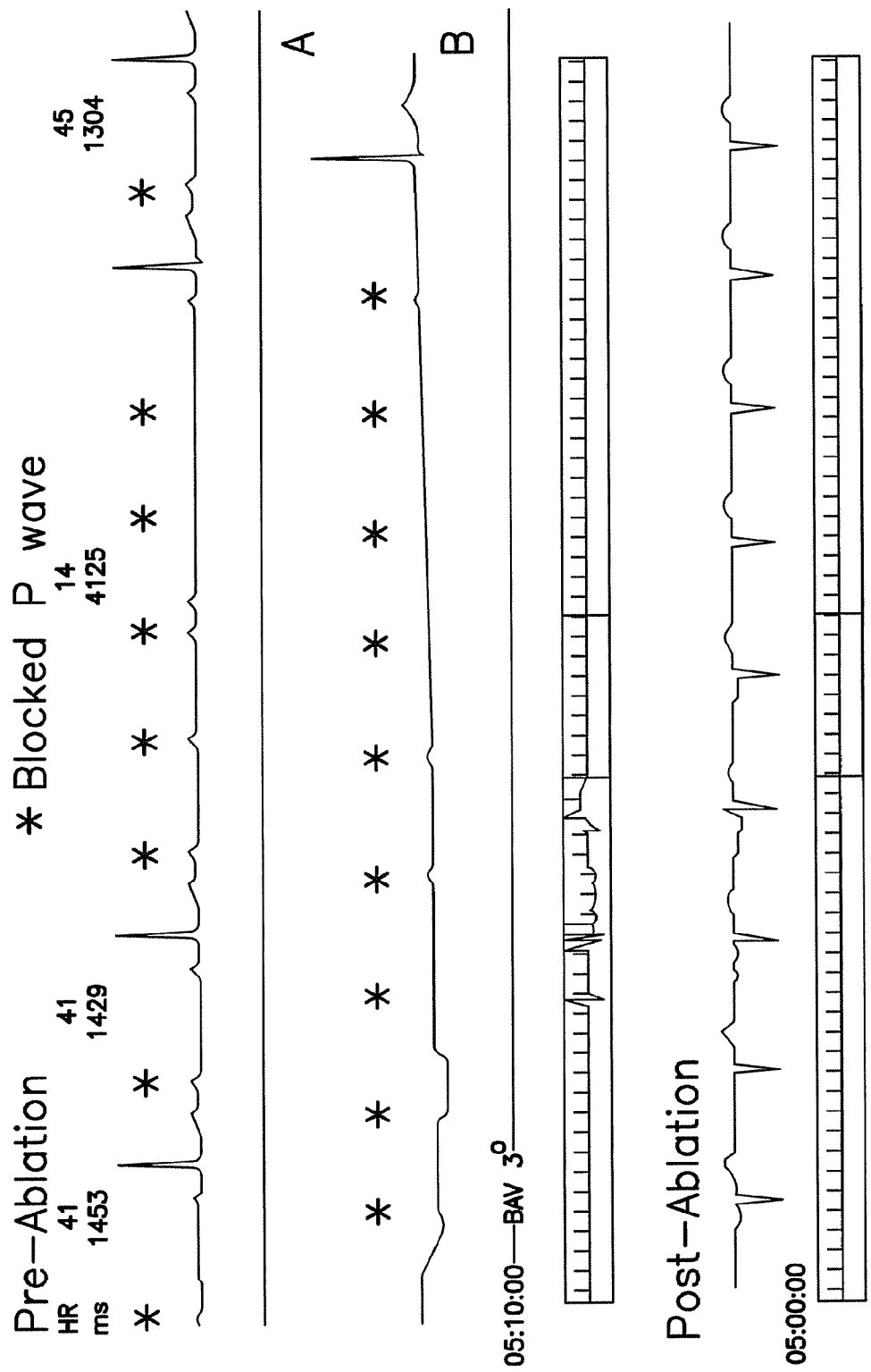
FIG. 11 shows Holter recordings showing the 24 h lowest heart rate pre- and one month post-cardioneuroablation in a case of functional intermittent high degree AV-block. In the pre-ablation Holter, there are periods of 5 and 9 consecutive blocked P waves. The patient was very symptomatic having syncope and dizziness being referred to pacemaker implantation. After the ablation she became asymptomatic.
Figure 12:
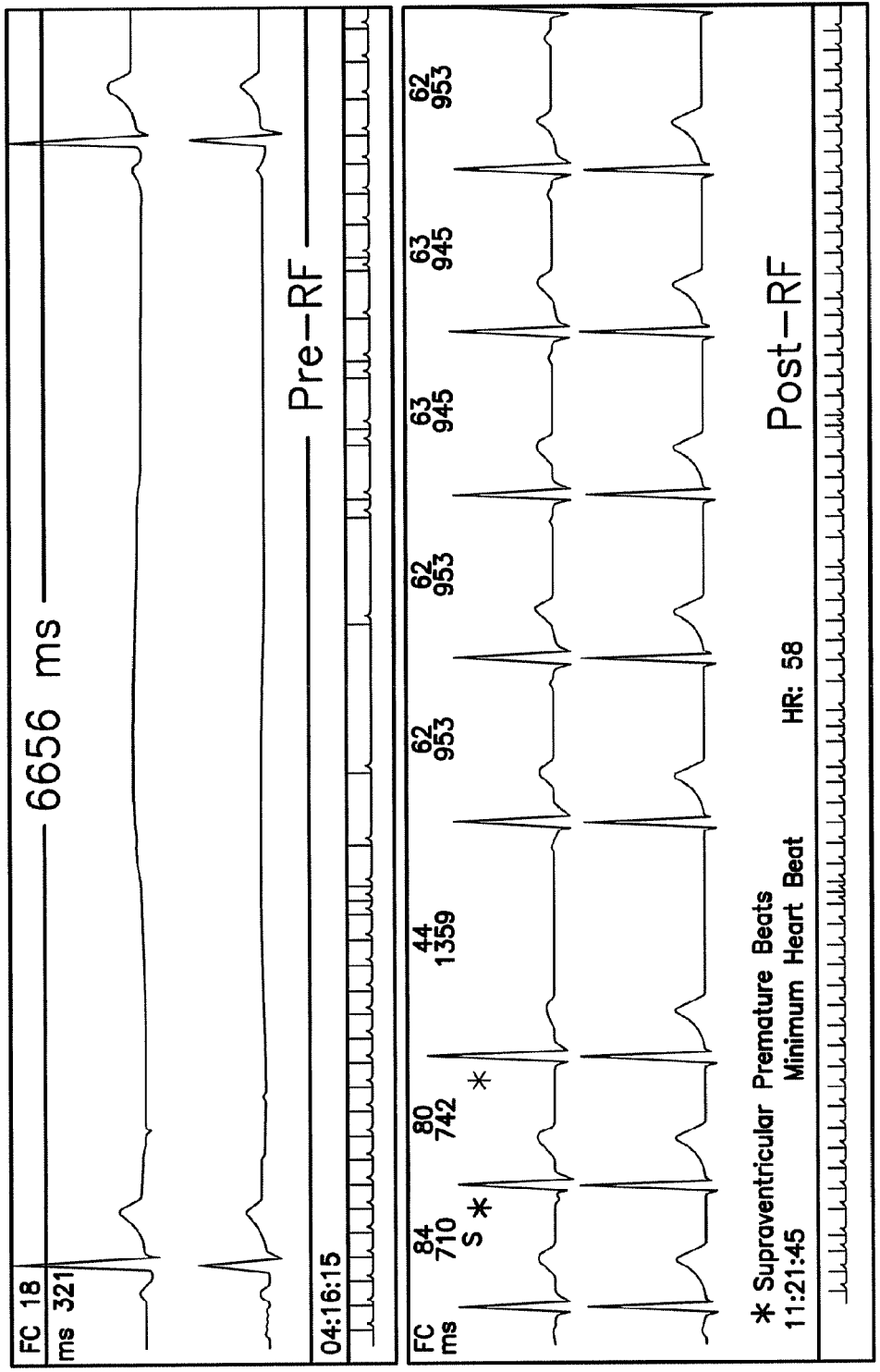
FIG. 12 shows a comparison of the minimum heart rate pre- and one month post-cardioneuroablation in a case of symptomatic sinus node dysfunction without apparent cardiopathy.

However, we have observed also that to get an extensive AV-nodal denervation, the ablation of all the points must be carried out in the left half of the left atrium endocardium presenting the spectral fibrillar pattern(s) as described and depicted herein. Thus, to get an efficient parasympathetic denervation of the AV node we must ablate the left atrium endocardium, the isolated right atrium approach being discouraged. (FIG. 10).

Sinus Node Dysfunction

This is the group having most of the pts. with some degree of cardiopathy. Regardless the total and/or corrected sinus node recovery time being abnormal in 11 pts. we considered they could be benefited by the cardioneuroablation because of the still good sinus chronotropic response during the stress-test. Despite having no important structural cardiopathy 9 pts. had brady-tachycardia alternating sinus bradycardia with paroxysmal AF. They were also submitted to the AF ablation with a new technique that does not interfere in the cardioneuroablation because it uses the same spectral mapping without line blocks and without pulmonary vein ablation. In this group both the bradycardia and the AF were eliminated.

Hocini and Haissaguerre et al. have observed reverse remodeling of sinus node function after catheter ablation of atrial fibrillation in patients with prolonged sinus pauses. This finding may be related to extensive atrial endocardial ablations aiming to get pulmonary vein isolation and line blocks that probably causes significant autonomic denervation.

In the whole group, an overall good response was confirmed by the control Holter that showed increase in the minimum and mean heart rate, significant reduction of the heart rate variability (from $183\pm53$ to $87\pm13$ ms, $p=0.003$), by the elimination of the pauses>2 seconds that previously presented a mean of $30\pm52$ in the whole group and eventually by the good clinical outcome. There was a trend to a better response of the patients having less sinus node disease. Notwithstanding all the patients had the sinus node recovery time normalized. These facts suggest that many times, even in mild sinus node disease it is possible to recover a great amount of the sinus function by reducing the vagal tonus. In this sense, this approach must be considered in cases of sinus node disease with pacemaker indication, but good response to atropine and without apparent cardiopathy.

The aim of this method was to achieve the parasympathetic denervation. Lesions of the sensitive and sympathetic fibers were undesirable despite being unavoidable. However, considering the anatomy of the cardiac autonomic nervous system only the postganglionic parasympathetic body cell was eliminated by the endocardial RF ablation. The sensitive and sympathetic postganglionic body cells are far from the heart and were preserved. The sympathetic and sensitive fibers eliminated by the RF have the capacity of recovery as well as having been observed in post-transplantation patients, refer to Limitations of this invention, below.

Apparently there is a large variability of the autonomic nervous system caused by anatomical, constitutional and pathological factors that make it difficult for a one pattern approach to be applied in all the cases. Also, this factor may be the origin of a significant diversity of results. Even for the patients having the control Tilt-test negative, its reproducibility is not enough to affirm they are cured. Despite the very good clinical outcome it is necessary that a long term follow-up occur to have definitive conclusions; The loss of the chronotropic competence in the early post-ablation period may cause some exercise intolerance that progressively disappears with the sympathetic reinnervation, with learning a new sympathetic modulation and with the physical conditioning. Obviously, as we are in the "learning curve", the technique was not the best for all the cases. There was an excessive care taken to avoid lesions on the specialized cardiac conduction system. The localization of the autonomic nervous entry was well defined by the spectral analysis. Nevertheless the para-cardiac ganglia ablation was based only in anatomical landmarks which may present important individual variety.

In the future, it is likely to have a specific marker by immunoscintilography or high precision intravascular ultrasound for very close mapping of these ganglia. The RF deliveries for para-cardiac ganglia modification were limited in energy to avoid extra-cardiac injury. However, with experience increasing higher energy could be considered aside employment of large surface or irrigated RF leads to promote deeper lesions with a corresponding higher ganglia denervation degree. Despite the reproducibility and the good clinical results, a larger number of patients should be treated and followed very well in order to achieve consistent conclusions.

The possibility of "partial cardiac denervation" with endocardial catheter RF-ablation may represent a new cardiology area with a large number of potential applications like providing curative therapy for neurocardiogenic syncope, carotid sinus syndrome, functional AV blocks, sinus node disease, nocturnal apnea syndrome, etc. In this study we demonstrate its potentiality to treat the functional bradycardias. The technique was easy, quite reproducible and efficient in the clinical control of neurocardiogenic syncope, of functional high degree AV blocks, and sinus node dysfunction, conditions which many times do not present satisfactory results when treated by medications and by pacing. The persistent parasympathetic denervation and the sympathetic reinnervation were demonstrated by the permanent modification of the heart rate variability in the chronic phase.

Despite the loss of the parasympathetic, the patients learned how to control the cardiac rhythm mainly by modulating the sympathetic nervous system without compromising the cardiac output and recovering the chronotropic competence.

The present invention provides a new method for paroxysmal AF RF-ablation targeting AF-nests. The 40 pts., 6 control pts. and 34 pts. having idiopathic drug-refractory paroxysmal or persistent AF were studied and treated. Two catheters were placed in the LA by transseptal approach. RF (30-40 J/60-70° C.) was applied in all sites outside the pulmonary vein (PV) presenting right-FFT-shift (AF nests).

Numerous AF nests were found in 34/34 AF patients and only in ⅙ control pts. (just in this case it was possible to induce AF despite an absence of AF history). The main fibrillar myocardium locations were: LA roof, LA septum, near insertion of superior PV, near insertion of inferior PV, LA posterior wall, RA near vena cava insertion, RA lateral and anterior wall and the right IA septum. Ablation of all AF-nests near PV insertion resulted in 35 PV isolation. After 9.9±5 months only 2 AF patients presented relapse of a different AF form (coarse AF) very well controlled with previous refractory medication. The AF was more frequent as the ratio fibrillar myocardium/compact myocardium increased.

The RF-ablation of AF-nests decreasing the Fibrillar/Compact myocardium ratio eliminated 94% of the paroxysmal AF patients in the FU of 9.9±5 months. The AF-nests may be easily identified by spectral analysis and seem to be the real AF substratum. Paroxysmal AF may be cured or controlled applying RF in several places outside the PV avoiding PV stenosis.

The renowned work of Haissaguerre et al. established that these muscular fascicles cause atrial premature beats, very fast atrial tachycardias and finally atrial fibrillation. This very important discovery caused the emerging of several techniques that comprise the modern AF catheter ablation therapy based on focal, segmental ablation or encircling pulmonary vein isolation.

Despite these very well accepted techniques some questions must be solved yet:

1. The pulmonary vein ectopic beats or tachycardias, and also atrial anatomical barriers may explain the atrial tachycardias, but they are not enough to explain the AF maintenance in most of cases;

2. Regardless of being rare, AF has been observed without pulmonary vein participation;

3. It is definitely accepted that the pulmonary vein premature beats are the most frequent AF triggers. However, the substratum is poorly known. Why do pulmonary vein ectopic premature beats cause AF in some patients while in others they may persist the whole life without causing any additional arrhythmia? Why may young people without any apparent cardiopathy have isolated AF? Why can many severe diseased atria survive without AF?

These questions suggest the presence of a consistent AF substratum apart from pulmonary vein triggers, which is common both in sick and in apparently normal heart. These observations made us hypothesize that the "fibrillar myocardium" niches—the "AF nests"—could be the real AF substratum depicting a new alternative to cure the arrhythmia apart from the triggers. Therefore, a goal of this invention was to achieve a new technique for AF catheter RF-ablation based on the elimination of the "AF nests".

To develop the present invention, 40 pts. were studied and treated, 34 pts. being highly symptomatic, having long lasting drug refractory AF, paroxysmal AF in 20 (59%) and persistent AF in 14 (41%) with very frequent episodes (from 2 episodes a month to an incessant form), mean age of 53.9±12 years (ranging from 22 to 70), 8 pts. (24%) females and 26 pts. (74%) males, and 6 control pts. (34.5±6 years) although having no AF history were submitted to general left atrium electrophysiologic procedures. There was no significant cardiopathy in any patient: mean ejection fraction=0.63±8 and mean left atrium size=41.1±7 mm. Mitral regurgitation was mild in 16 pts. (47%) and moderate in 5 pts. (14.7%). 12 pts. (35.3%) had history of mild to moderate arterial hypertension. There was no significant coronary disease or dilated cardiomyopathy. All patients were taking high antiarrhythmic doses of amiodarone (21 pts.), sotalol (19 pts.), propafenone (12 pts.), beta-blocker (10 pts.), quinidine (7 pts.), dysopiramide (8 pts.) either isolated or associated (2 or 3 drugs). 17 patients were under regular warfarin use keeping the mean prothrombin time in 2.1±0.3 INR. 12 patients were taking 100 mg of aspirin a day. None of these cases had had a history of a thromboembolic episode. 8 patients had diabetes mellitus controlled by oral anti-diabetic drugs.

Before the procedure, all AF patients were studied by magnetic resonance in order to evaluate the pulmonary veins anatomy. All pts. presenting risk factors like hypertension, diabetes or mild atrial dilatation were treated with warfarin during one month replaced by subcutaneous low molecular weight heparin two days before the ablation. All patients provided a written informed consent. The procedure began with endovenous general anesthesia being the ventilation controlled by Drager Cicero E M. The heart rate, oximetry, blood pressure, pletismography, peripheral perfusion, capinography and respiratory gases were monitored by the Merlin Agilent/Philips polygraph. Brain functions were monitored by direct measurement of the awareness level keeping the Bi-spectral index between 40 and 50 (BIS Aspect A-1000), and through cerebral oximetry measured by frontal infra-red spectroscopy (NIRS-Cerebral Oxymeter Somanetics-INVOS) targeting the $sRO_2 \geqq 75\%$ from the pre-induction levels. A complete trans-esophageal echocardiogram was performed seeking for thrombus or "spontaneous contrast" before the transseptal and electrophysiological catheterization.

In 8 pts. (21%) that presented AF, a transthoracic cardioversion (biphasic 30 J to 100 J) was performed, recovering the sinus rhythm. Four electrophysiological catheters were placed (coronary sinus, His bundle, right atrium and right ventricle) through subclavian and femoral venous punctures, carrying out the conventional electrophysiological study. Finally, one spiral lead from St. Jude Medical, Inc., St. Paul, Minn., namely, the SUPREME™ catheter (14 pts.) and one EPT Blazer 7F (EP Technologies, Inc) (34 pts.) were placed in the left atrium, through one patent oval foramen in 2 pts. and through transseptal puncture in 32 patients, by using 2 introducers DAIG SL-1 and SL-2 8F. Systemic anticoagulation was achieved with intravenous 5-10,000 IU heparin and additional 1,000 IU each according to the coagulation activated time. The electrophysiological mapping was accomplished with a 32 channel polygraph TEB-32 with special software for spectral analysis (Pachon-TEB2002) and the graphical ScopeDSP FFT software from Iowegian International Corporation, Iowa, USA version 3.6a and SigView-1.9 (from SignalLab a privately-held German company).

Figure 18:
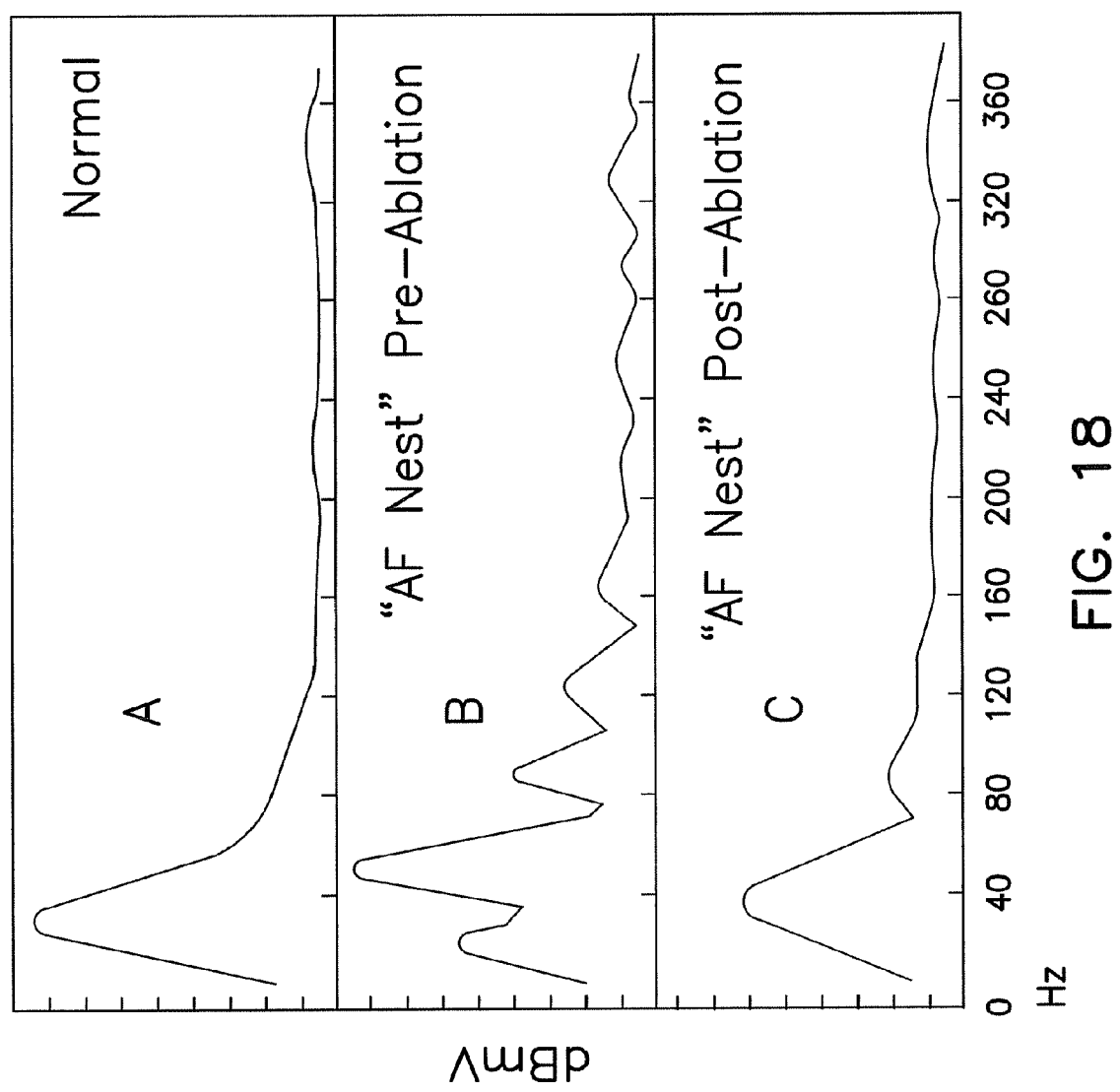
FIG. 18 shows a spectral analysis, using fast Fourier transform (FFT), of the "compact" myocardium (A) and "AF nest" potentials found in the left atrium roof before (B) and after RF ablation (C). The RF blunts more significantly the frequencies above 80 Hz, thus rendering the spectrum of the "AF nest" similar to that of the "compact" myocardium.

The study began at the endocardial surface of the left atrium near the left pulmonary veins insertion, with the ablation of all the potentials that presented right-Fourier-shift (AF nests) during sinus rhythm and during pacing of the distal coronary sinus. The same procedure was repeated for the left atrium roof, for the left atrium wall near the right pulmonary veins insertion, for the left atrium posterior wall and, finally, for the left surface of the interatrial septum. Similar procedure was repeated for the right atrium eliminating all AF nests, taking special care to avoid lesions in the sinus and AV nodes. Ablations were performed with the Thermo-Controlled Biotronik MDS ablator with 30 to 40 J during 15 to 20 seconds, 60 or 70° C. In each AF nest, RF was applied only for shifting the FFT toward the left, FIG. 18. The spiral catheter was used only for checking the frequent pulmonary vein isolation during the ablation of the AF nests near the pulmonary vein insertion showing its relation with the venous myocardium. Intentional electrical venous isolation was not intended. The procedure was suspended as soon as no more AF nests could be found. Oral anticoagulation was maintained for 3 months. Statistical Analysis observed continuous variables were expressed as mean±one SD and were compared by Student's t test. A p≦0.05 indicated statistical significance.

The effect of the present invention can be seen from the results of the Spectral Analysis of the Compact and Fibrillar Myocardium. The compact myocardium presented a homogeneous spectrum with a fundamental frequency ranging between 50 Hz and 75 Hz (mean 59.6±11.4 Hz), FIG. 13-2A. Most AF nests (fibrillar myocardium) presented a fractionated spectrum with 3 to 6 significant components (mean 3.6±0.8), FIG. 13-2B. The fundamental frequency ranged from 15 Hz to 87 Hz (mean of 34.8±18.1 Hz) with the first most significant harmonic between 38 Hz and 137 Hz (mean of 81.1±27.3 Hz). The remaining harmonics presented mean frequencies of 174.2 Hz and 252.8 Hz, respectively. After ablation, the fibrillar myocardium showed remarkable reduction of the harmonics but only moderate reduction in the amplitude of the fundamental frequency, resulting in a left frequency shifting, with the final spectral curve similar to that of compact myocardium, FIG. 18.

In the control group no typical AF nests were found except in one patient. AF induction was possible only in this case despite having no history of spontaneous AF. In the PAF group AF nests were very frequent in all pts. They were treated a mean of 40.9.quadrature.11.8 (range 18-61) AF-Nests by patient being 9.7 times more frequent in the left than in the right atrium. They were located mainly in the following places:

1. Left atrial endocardium:
  a. Near the left superior pulmonary vein insertion in 31 (91.1%) and near the inferior in 23 (67.6%) patients;
  b. Near the right superior pulmonary vein in 30 (88.2%) and near the inferior in 18 (52.9%) patients;
  c. Left atrium roof in all patients (100%);
  d. Left surface of the interatrial septum in 31 (91.1%) patients;
  e. Left atrium posterior wall in 20 (58.8%) patients;
2. Right atrial endocardium:
  a. Right surface of the interatrial septum in 15 (44.1%) patients;
  b. Right lateral wall and crista terminalis in 16 (47%) patients;
  c. Right atrial wall near the insertion of the veins cava (except the sinus node area) in 21 (61.7%) patients. Non-intentional electrical isolation of 35 pulmonary veins, 6 superior and 3 inferior vena cava were observed during the ablation of the AF nests on the atrial wall near the venous insertion.

At ablation, two atypical left atrial flutter were observed, one case was abolished by RF application and the other reverted by cardioversion. Another 3 cases of atypical flutter were observed on the first and second post-ablation days, and were treated with endovenous amiodarone (2) and external cardioversion. Finally, a different kind of AF was also observed, which occurred in 6 cases, in the first week pos-ablation, which were a kind of coarse AF with larger "f" waves and lower frequency than the AF before ablation. They were solved with temporary low doses of amiodarone lasting one to three days of treatment. All these arrhythmias were no longer observed after the healing phase. The mean follow-up was 9.9±5 months. After the healing phase, 32 paroxysmal or persistent AF patients are in sinus rhythm with no episode of AF (94.1%). Only two patients presented AF relapse (5.9%) responsive to previous refractory medication. Holter monitoring was performed in 28 patients. The most significant finding was the presence of frequent atrial premature beats in 6 and rare atrial premature beats in 26 patients. Furthermore, very short episodes of non sustained atrial tachycardia were observed in 5 cases.

Despite the very low significance of the arrhythmias, 14 (41.1%) patients are taking low doses of previously ineffective antiarrhythmic drugs (amiodarone 100 mg/day [12], sotalol 40 to 80 mg/day [7]) for palpitations and/or blood pressure control. Two pericardial effusions occurred in cases with difficult transseptal puncture due to anatomical variation being one clinically treated and the other solved with pericardial drainage. No other complications were observed. The mean time of radiation, including the transseptal puncture, was 44.1±11.2 minutes.

Discussion and Comments

Figure 13:
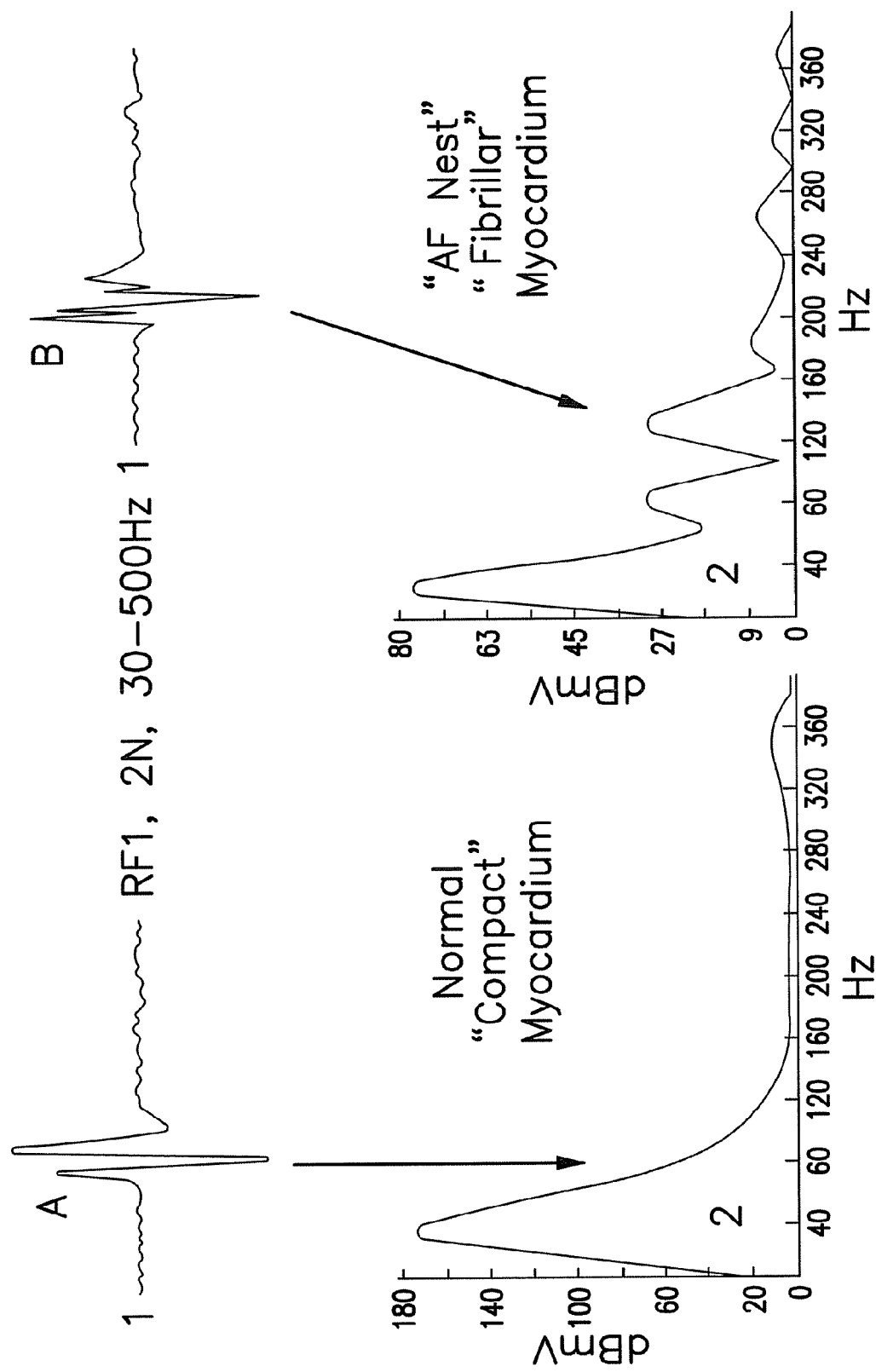
FIG. 13 shows a comparison of the spectral analysis of the left atrium endocardial potentials (1A and 1B) showing in A the "compact" and in B the "fibrillar" myocardium (posterior wall and left atrium roof, respectively). It can be observed that the "compact" presents one fundamental frequency (2A) and higher power than the "fibrillar", which presents at least 3 prominent frequencies (one fundamental and two important harmonics, 2B). Although in the time domain (1A and 1B) the endocardial potentials are similar there is significant difference in the FFT-spectral analysis (frequency domain, 2A and 2B).

In this study, using the spectral analysis through the fast Fourier transform (FFT), it was possible to clearly identify 2 kinds of atrial myocardium with very important electrophysiological differences, which we have named as compact and fibrillar, FIG. 13. The former, normal and predominant, shows a homogeneous spectral shape around the fundamental frequency, FIG. 13-2A. In contrast, the latter shows lower amplitude, segmented and heterogeneous spectrum, FIG. 13-2B. Since the harmonics are gathered in 2 to 5 groups of relative high amplitude, the fibrillar myocardium is characterized by a rightshift of the spectrum. The FFT allows us to conclude that the fibrillar myocardium may be composed of several myocardium strands with few lateral connections, presenting dispersion of the conduction speed.

Figure 14:
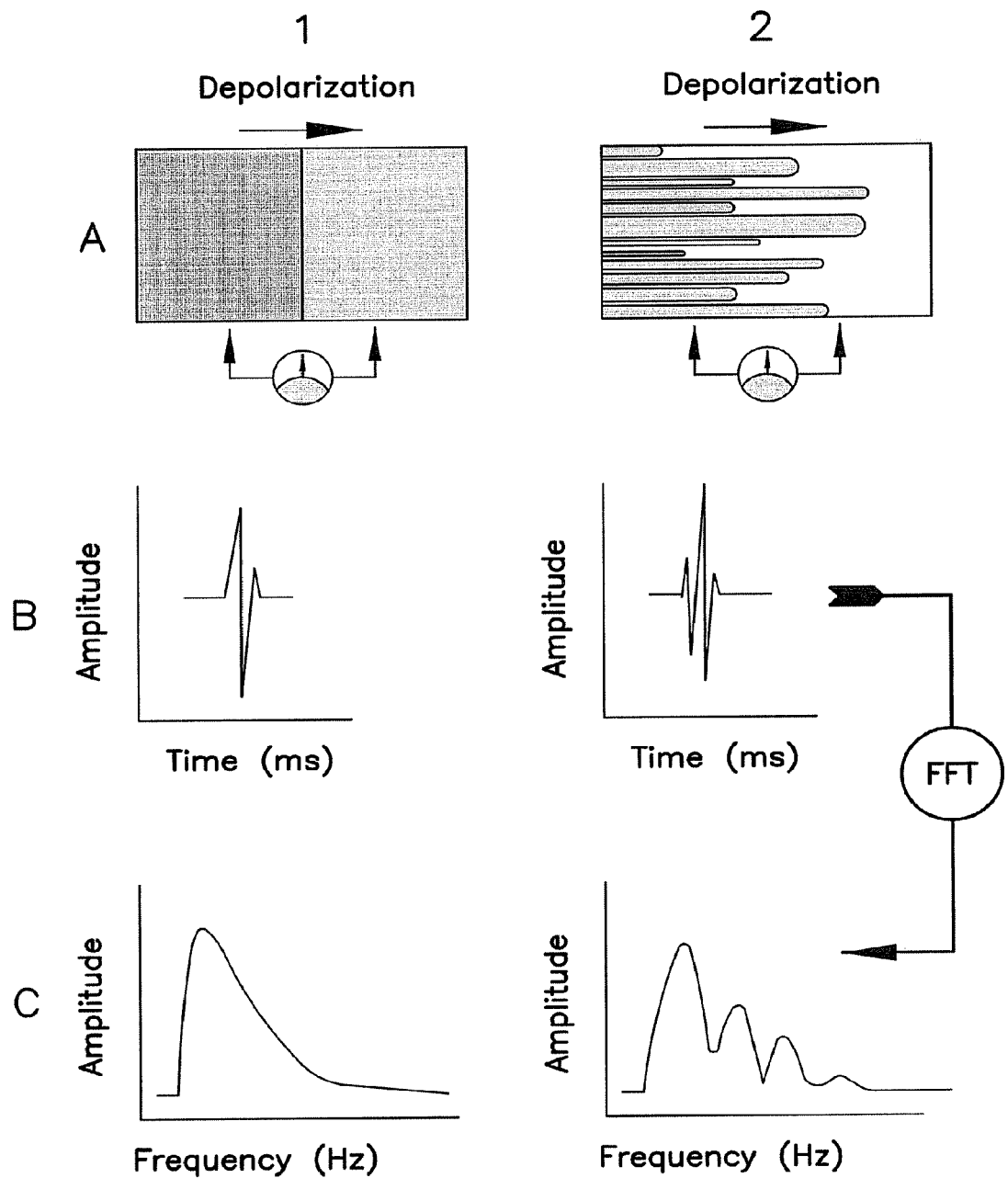
FIG. 14 is a diagram of the activation wave in the "compact" (1) and "fibrillar" (2) myocardium. In the former, the activation moves forward in a homogeneous way, keeping all cells inphase (1A). The endocardial potential usually shows bi- or tri-phasic shape (T1, time domain). The study in the frequency domain (FFT) shows a homogeneous profile around one fundamental frequency (1C, frequency domain). Inversely, the "fibrillar" myocardium works similarly to many cell bunches. The wave front is irregular because of the out-of-phase activation between the several strands of cells (2A). In the time domain, this generally results in a polyphasic wave (2B), and in the frequency domain it shows less amplitude and a heterogeneous profile with the fundamental frequency followed by a variable.

Thanks to the conexins, the compact myocardium—which is the predominant pattern—is composed of tightly connected cells, Table 2. This very well organized structure works like one cell due to the intercalated discs. Its conduction is homogeneous with a predominant wave front and, in absence of barriers presents similar speed in any direction (isotropy), FIG. 14-1A. As a rule, the resulting potential is fast, bi or triphasic, FIG. 14-1B. The cells work in-phase, reacting in a organized sequence that results in a uniform spectral pattern, FIG. 14-1C. The fibrillar myocardium is much less frequent and is located in some specific regions in the atrial wall (AF nests), Table 2. Apparently, a fibrillar myocardium is more primitive, and seems to have transitional features between nervous, vascular walls and atrial myocardium. In contrast to the compact, a fibrillar myocardium works like a bunch of loose cells.

Probably the lateral connections are scarce promoting a longitudinal conduction speed higher than the transversal one (anisotropy), and heterogeneous wave front conduction. High speed filaments are side by side with others of less speed, FIG. 14-1B, resulting in an out-of-phase conduction and a polyphasic potential, FIG. 14-2B. The spectrum of this tissue is typically very fractioned, suggesting it is composed of relatively independent fascicles. We conclude it has much less conexins than the compact FIG. 14-2C. The electrophysiological features of this tissue permit the highest response rate among the cardiac cells being the most probably substratum for the AF maintenance.

Location of the Compact and Fibrillar Myocardium By means of spectral analysis, the narrow areas of fibrillar myocardium—AF nests—could be found easily. Although there was a significant variation among patients, these places were usually found in the atrial wall near the pulmonary veins insertion, more frequent in the superior ones. Frequently it was observed inside the pulmonary veins. A very interesting aspect was the great amount of AF nests in the roof of the left atrium, FIG. 13-B in all patients. Another place with great prevalence of AF nests was the interatrial septum, FIG. 15 that presented a dilatation in one patient and a small aneurysm in another.

In these cases, numerous AF nests were found in the whole left surface of the interatrial septum, being less frequent in the right. This finding suggests that the distention of the atrial myocardium likely converted the compact into fibrillar myocardium, probably by detaching inter-cellular connections. This phenomenon could explain one acquired origin for the fibrillar myocardium, caused by the stretching and/or degeneration of the compact one. Less frequent AF nests were found in the right atrium. The more commonly involved places were the junction of superior vena cava and right atrium, the right surface of the interatrial septum in the posterior area and near fossa ovalis and the crista terminalis. An essential trait is that both the sinus and the AV nodes areas present frequency spectrum very similar to the fibrillar myocardium (probably due to the nervous origin) being necessary special attention for not damage them.

Our main purpose was to find and abolish the AF substratum without line blocks. In this sense, the following observations suggest the fibrillar myocardium and the AF nests are the real AF substratum:

1. In this series, the more frequent the AF episodes, the more numerous the AF nests, found in 34/34 AF patients (100%) and only in ⅙ of the control group (16.7%);

2. Nearly all AF patients (94.1%) were cured or very well controlled with low antiarrhythmic dose after ablation of all AF nests that could be treated;

3. In two pts. AF was induced persisting only in the right atrium, the left one remaining in secondary tachycardia (limited by its refractory period) after the treatment of all the left atrium "AF nests";

4. It was also observed that during AF, the AF nests presented activation frequency higher than any surrounding atrial myocardium.

Figure 15:
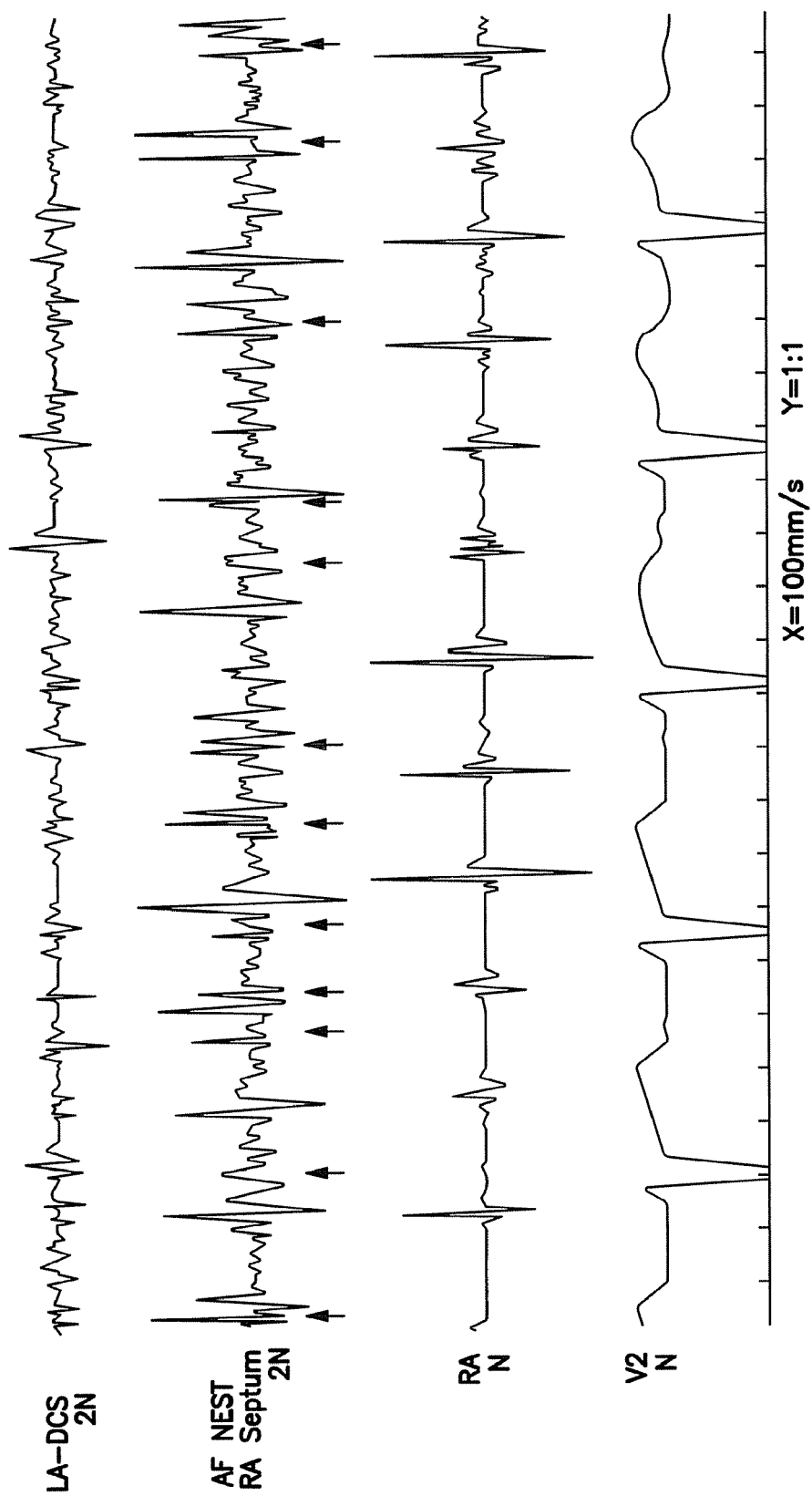
FIG. 15 shows in an upper strip a series of atrial potential recordings. The first strip shows the left atrial potential recording (distal coronary sinus-LA-DCS). The second and third strips were obtained at the right atrium, RA (in the second strip the lead is positioned at one "AF nest" on the right side of the inter-atrial septum in the posterior region. In the third strip, the lead is positioned at the RA free wall). The lower strip shows the standard V2 lead. AF was induced with atrial programmed stimulation in the right atrium. In this case the highest activation rate is observed in the right atrial "AF nest". The very fast and successive activations pointed out by arrows are typical of tissues that present very short refractory period, out-of-phase conduction, reflection and micro-reentry. Comparing the "fibrillar" myocardium (2nd. strip, "AF nest") with the "compact" one (3rd. strip-normal RA free wall) the number of activations has been observed to be higher in the former.

In FIG. 15 AF was induced by programmed stimulation, after placing leads in one AF nest (in the posterior right interatrial septum), in the coronary sinus, and in the right atrium wall. It may be clearly observed that the AF nest presents the highest frequency and the most out-of-phase and disorganized activation. The shortest interval between two consecutive near-fields shows that the refractory period of the AF nest is much smaller than that of the compact myocardium. These data match with the findings of Haissaguerre et al who have demonstrated the very short refractory period of muscular pulmonary vein sleeves (less than 100 ms). Oral et al. have reported AF ablation during arrhythmia, seeking for the fastest activation rate in the pulmonary veins sleeves (probably fibrillar myocardium inside the veins).

Figure 3:
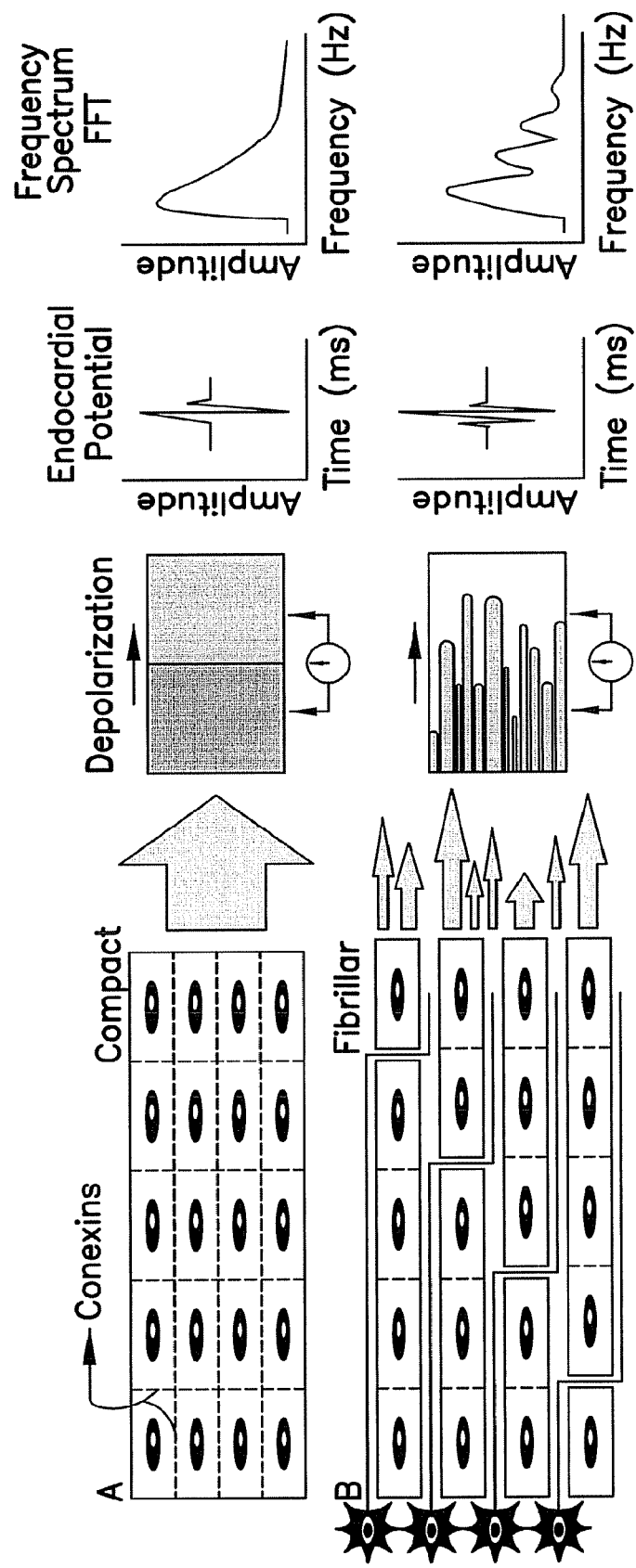
FIG. 3 is a schematic diagram of the interface between the autonomous nervous system and the atrial myocardium. Apparently the penetration of the nerve fibers changes the myocardial conduction and the frequency spectrum of the endocardial potential which shifts from the compact conduction (A) pattern to the fibrillar pattern (B). The conexins are represented as small white bars between the cells. In the portion of FIG. 3 captioned as "A" which depicts an interpretation of the working normal myocardium is depicted with very well connected cells (compact myocardium) that result in an electrical conduction with homogeneous spectrum; and the captioned as "B" which depicts an interpretation of the neuro-myocardium interface. In this point the myocardium behaves like a group of relatively independent cellular filaments because of the neural fibers interposition. The fibrillar pattern can be identified by the typical highly segmented heterogeneous spectrum with frequencies deviation to the right (fibrillar myocardium). By using specific band-pass filters it is feasible to identify both kinds of myocardium with high accuracy even in the time domain.
Figure 16:
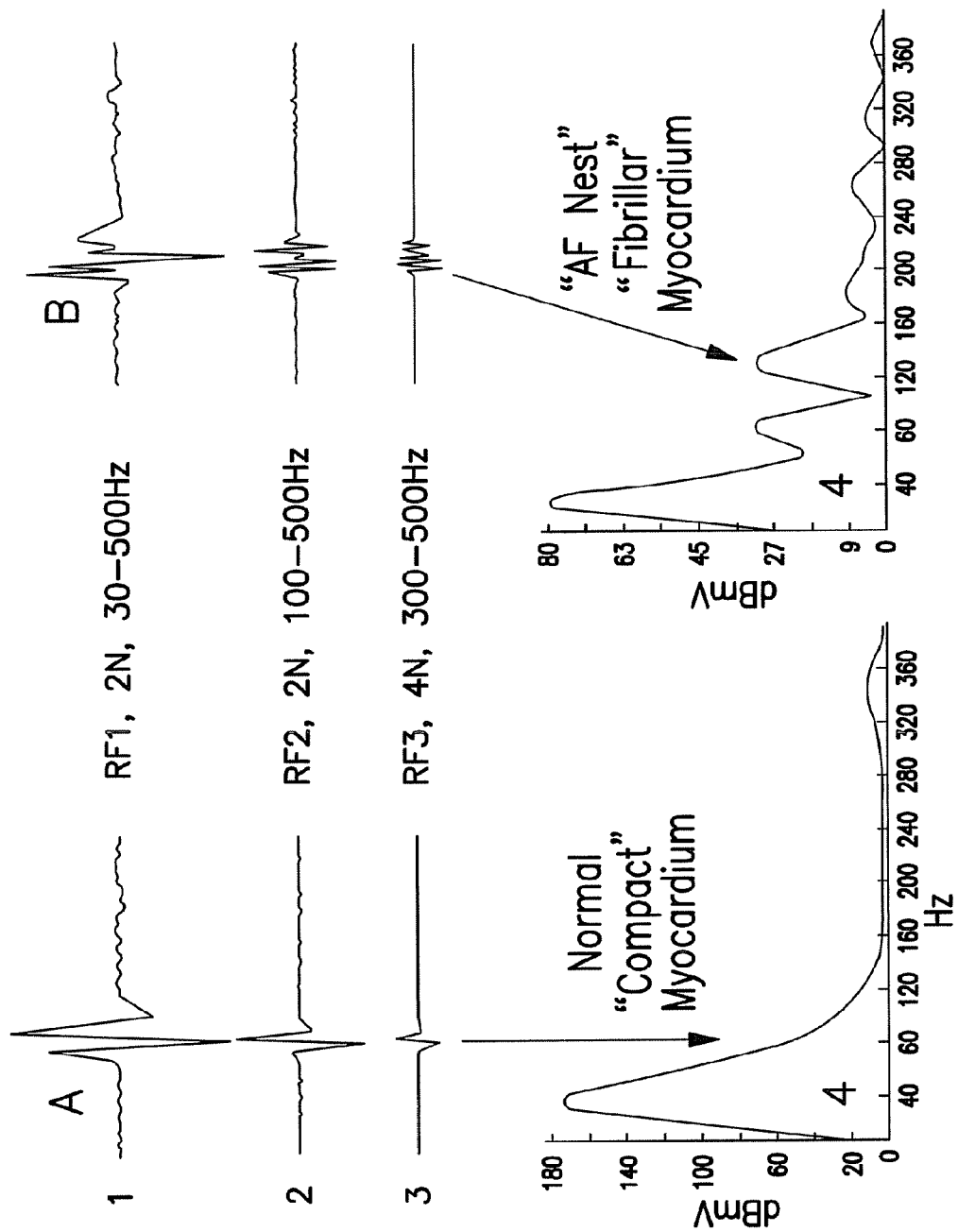
FIG. 16 shows the atrial potentials recorded in time domain (1, 2 and 3) and in frequency domain (4) from the left atrium. A: "compact" myocardium in LA-interatrial septum; B: "fibrillar" myocardium from the LA roof. Spectral analysis shows very different profiles, with a homogenous "compact" spectrum (A4) versus a "right shifted" and coarsely segmented "fibrillar" spectrum (B4), despite the similar and polyphasic conventional filtered atrial potentials (A1 and B1). The great difference appears in high frequency channels 2 and 3, which show high fractioned complexes in the "fibrillar" myocardium ("AF nest"), B2 and B3. Therefore, time domain with high frequency filters may be used to map the "fibrillar" myocardium that must be ablated.

We have observed similar behavior of the AF nests in the atrial wall. Hence, it seems that the very early premature beats originated in the pulmonary veins or in the atrial wall enter the AF nests, being multiplied by reflection, micro-reentry or mainly by "electrical resonance" originating and maintaining the AF by feed-back among several of them. The elimination of AF nests or the isolation by creating line blocks make the AF maintenance more difficult;

5. It has been shown that patients who have undergone pulmonary vein isolation present AF control in spite of atriopulmonary vein conduction recovering (up to 70% of cases). In other cases there has been observed AF recurrence despite complete atrio-venous electrical block, suggesting that in some cases the AF treatment may not be totally dependent of the complete pulmonary veins isolation;

6. In this series, many AF nests were observed near the pulmonary veins insertion. Conventional RF over these areas, aiming at encircling or segmental isolation of pulmonary veins, ablating great amount of compact and fibrillar myocardium, decreases the number of AF nests. In these cases the AF control may have been obtained also by AF nests elimination. This effect may be more significant in cases undergoing multiple procedures;

7. In one patient the AF was caused by numerous AF nests located in the interatrial septum, which had a remarkable dilatation. The ablation of these points was enough to cure the arrhythmia;

8. In five control patients we did not find AF nests and could not manage to induce AF with atrial stimulation. However, in one control patient (a 22 year-old man) presenting AF nests, sustained AF was induced despite having no AF history;

Studying a large number of AF nests potentials by using the fast Fourier transform we have developed a simplified spectral analysis by filtering the RF-catheter signal in three channels of the conventional polygraph −30 to 500 Hz in the first, 100 to 500 Hz in the second and 300 to 500 Hz in the third, FIG. 16. We have observed that the AF nests tend to present relatively delayed high amplitude in the 3rd channel with characteristic polyphasic high frequency potentials in the 2nd and in the 3rd channel. Typically, the 3rd channel potential lasts more than 30 ms when measured from the beginning of the 1st channel, FIG. 16-3B.

Figure 17:
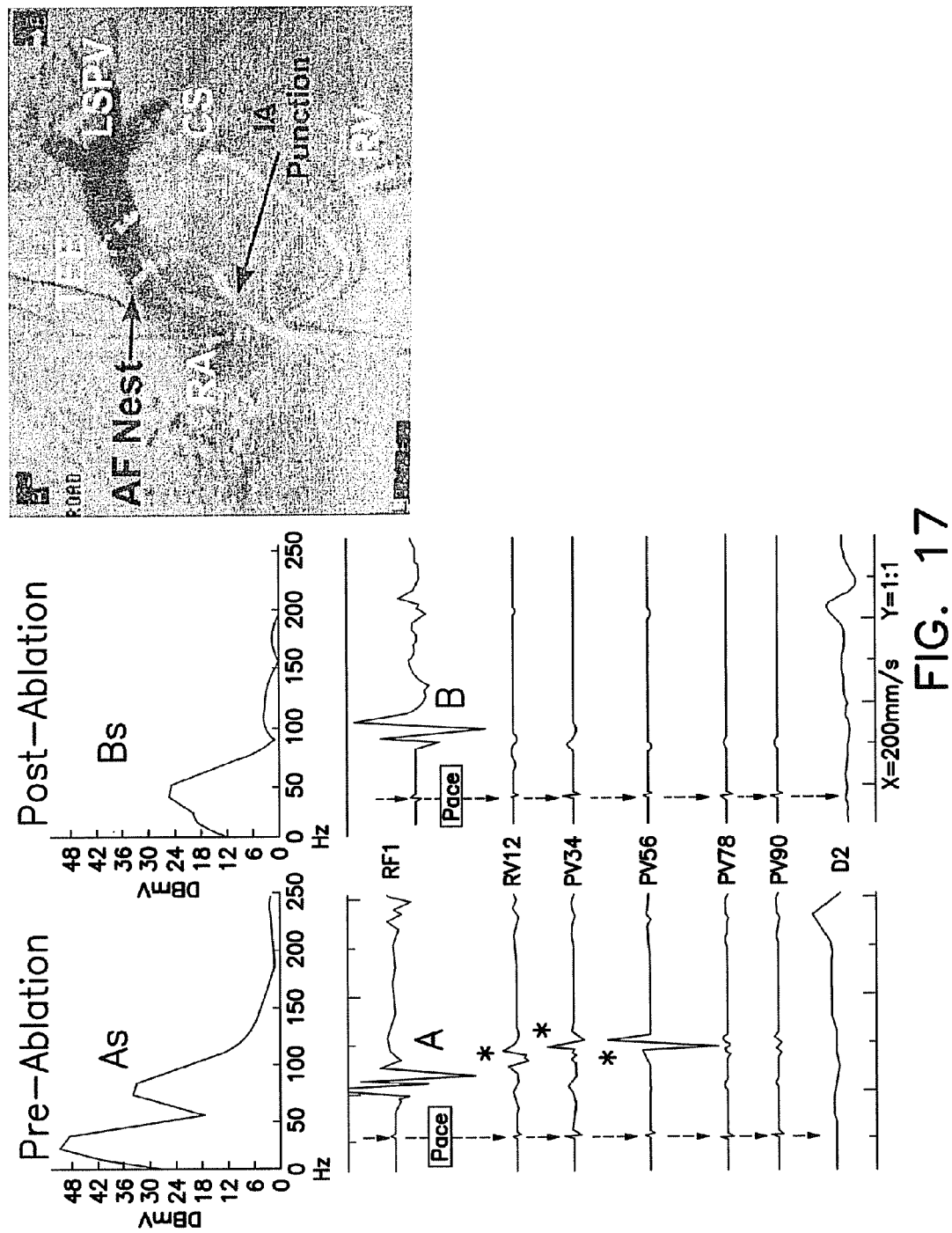
FIG. 17 shows on the left: a recording of the electrical activity of an "AF nest" in the left inter-atrial septum, close to the LA-roof, before (A) and after (B) RF ablation. The As and Bs are respectively the spectral analysis of the A and B potentials obtained by FFT. The five identified channels with PV are connected to the five dipoles of a spiral lead, placed inside the initial portion of the same pulmonary vein. A vein potential of great amplitude is observed in 1-2, 3-4, and 5-6 (*) dipoles. After RF ablation of the "AF nest" in the atrial left wall, outside the pulmonary vein, we can observe (on the right) the electrical "isolation" of the vein with disappearance of the vein potentials. The "AF nest" lost about 50% of the spectral power and there was the almost complete disappearance of the signs above 100 Hz from the "AF nest" (Bs). In that way, from the spectral point of view, the RF converts the "fibrillar" myocardium into "compact-like", avoiding the AF installation or making it less probable. On the right: Radiological road-mapping during spectral AF ablation showing the RF-catheter in one "AF nest" in the left inter-atrial septum, therefore outside the pulmonary vein. TEE: transesophageal echocardiographical probe, CS: coronary sinus; LSPV: left superior pulmonary vein, IA: interatrial, RA and RV: right atrium and ventricle.

The location and the treatment of the AF nests were accomplished with the same catheter. The spiral catheter, placed in pulmonary veins, was used to demonstrate that the elimination of the AF nests near pulmonary veins resulted in many veins isolation, FIG. 17. This fact suggests that the natural muscular fibers dispersion in the atrium-vein transition probably favors the appearance of fibrillar myocardium building up congenital or natural AF nests.

The RF was applied outside the pulmonary vein in pulses of 30 to 40 J during 15 to 20 seconds, with the temperature limited to 60 or 70° C. (depending on the proximity of the pulmonary veins). The purpose was to get the elimination or significant attenuation of the high frequency AF nest potentials in the 3rd channel. The low frequency presents only a discrete amplitude reduction, left shifting the resulting spectrum towards the normal shape. The Fourier transform shows that, after ablation, the great amount of segmented harmonics above 80 Hz from the AF nests is strongly reduced or eliminated being the fundamental frequency less affected. As a result, the partial RF ablation of the fibrillar myocardium tends to convert its spectrum into that of the compact, FIG. 18.

Figure 19:
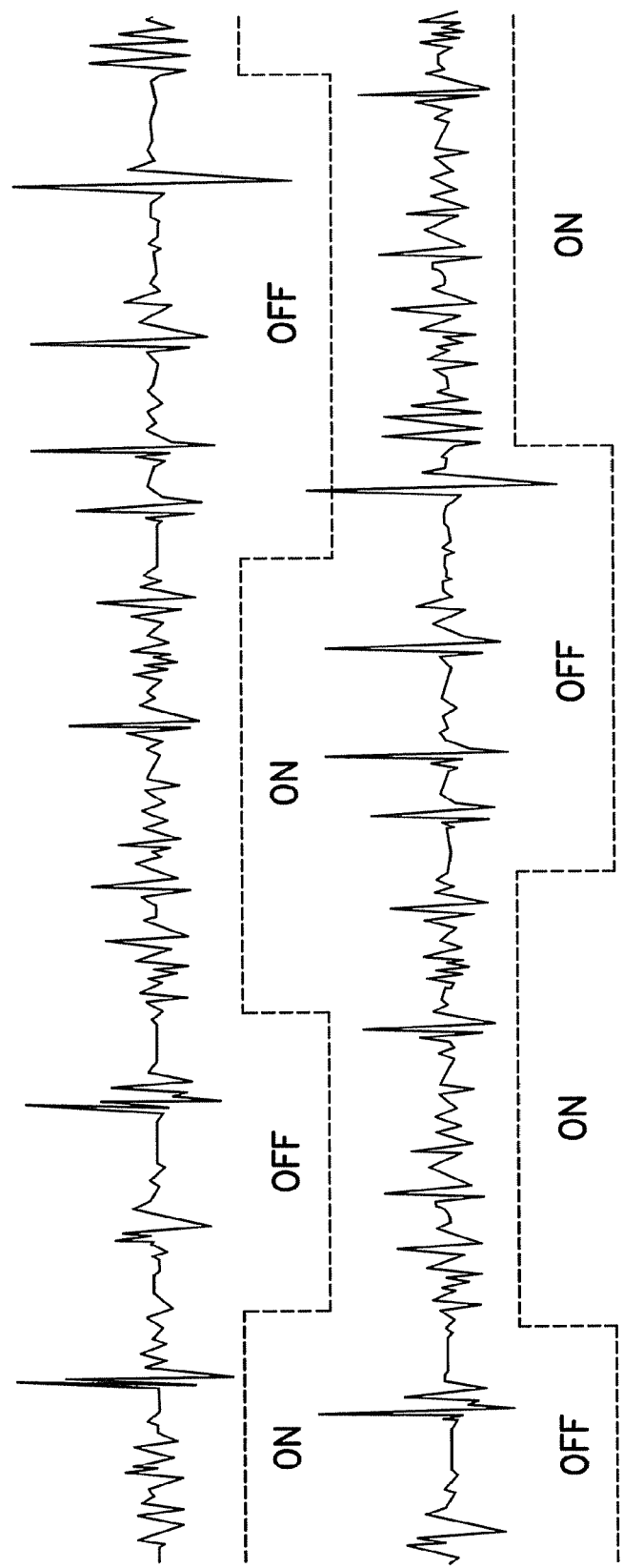
FIG. 19 shows the dual state behavior commonly observed in the AF Nest during AF. The "on" is the "active state" (resonant behavior featured by repetitive, disorganized and decremental responses—baseline not well defined). The "off" is the "passive state" (bystander behavior—in this moment the AF Nest only await for external stimulation—baseline well defined). If there are at least two AF Nests switching these states in out-of-phase condition the AF is maintained because when one is passive the other being active stimulates the condition. However, if there is a concurrence of the bystander state of the all AF Nest the AF suddenly stops.

Stimulating the atrium with progressive high frequency energy we have found a very interesting difference in the compact and fibrillar myocardium behavior. The former resists very well to frequency increase without electrical disorganization ("Bystander Behavior"—the passive state), FIG. 15-RA, while the latter presents cyclic high frequency disorganization ("Resonant Behavior"—the active state), FIG. 19. The "Resonant Behavior" is a repetitive and decremental electrical activity, similar to an energized "tuning-fork". In this study it was observed that to be maintained, the AF needs at least one AF Nest all the time in the "resonant" state or several cyclic AF Nests, out-of-phase oscillating from the "bystander" to the "resonant" state. In this way, when one AF Nest is in the "passive state" (bystander) it is activated by another AF Nest that is in the "active state" (resonant). The AF only spontaneously reverts when, within a short time fraction, all of the AF Nests coincide at the "bystander" condition. This physiopathology understanding allows us to ablate the AF during the arrhythmia. In this case we have sought for the "resonant" areas. As the compact myocardium does not present this state it represents one AF Nest. Thus, after ablating several resonant areas during AF we eliminate the AF reverting it to the sinus rhythm.

Positive Aspects of this Methodology:

1. This method allows AF ablation with high probability of cure or AF control without seeking for pulmonary vein premature beats. Besides being less time-consuming, it seems to be highly effective, regardless of the erratic presence of pulmonary ectopic activity.

2. The ablation outside pulmonary veins avoids the risk of pulmonary stenosis.

3. Short pulses of RF without destruction of large amount of tissue—just aimed at shifting the spectrum (FIG. 18)—and without line blocks reduce the lesions, decrease the perforation and pericardial tamponade risks and minimize thromboembolic hazard, as well as the iatrogenic arrhythmia caused by incomplete line blocks.

4. The procedure duration and cost are also reduced, since additional mapping procedures like electroanatomic and venous transverse mapping were not necessary.

5. As AF induction and cardioversion are not performed, complications and myocardial damage are less likely to occur.

6. The total or partial treating of the substratum have eliminated the arrhythmia, even when triggering factors persist or appear.

7. The initial experience, despite being in the learning curve and without using navigation-aid tools, is showing very good results.

8. The need for only one catheter decreases risks and costs.

Figure 20:
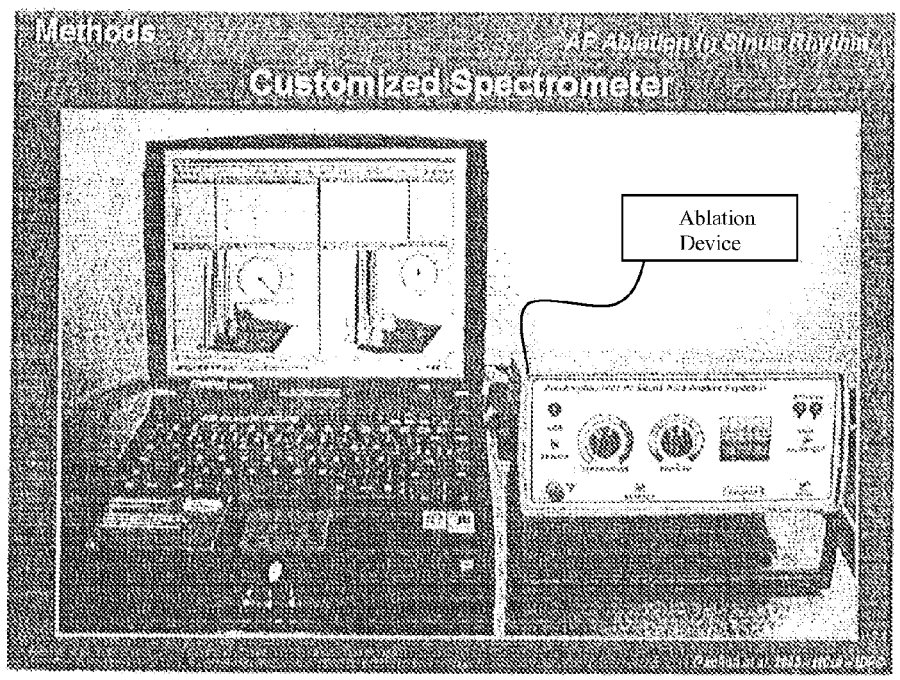
FIG. 20 is a photographic view of the computer (left) and of the Spectral Amplifier connected at the workbench. The method is being currently used for "AF Spectral Ablation during Sinus Rhythm" and for another method named "Cardioneuroablation" and for investigating the physiopathology of these arrhythmias.
Figure 21:
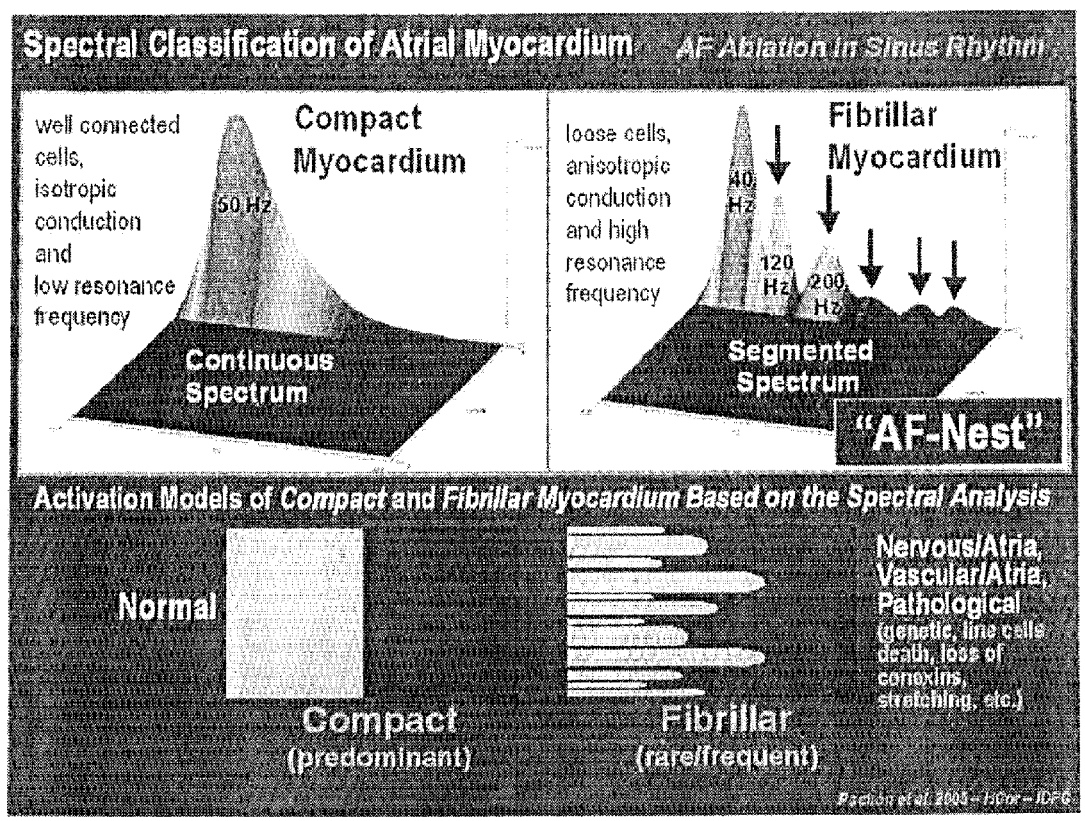
FIG. 21 is an example of two spectra obtained by this method. On the left there is one spectrum of the compact myocardium. On the right one example of the "fibrillar myocardium" forming one "AF-Nest". The "AF-Nests", discovered by this method, are the real substratum of the atrial fibrillation and are also the regions of innervation entry in the atrial wall.

9. Despite not having been tested in this series, this methodology using the spectral analysis has a great potential to be applied for ablation even during AF (FIG. 20, FIG. 21).

10. Finally, this new methodology identifies and defines a new concept of the AF substratum and physiopathology.

Negatives Aspects of this Methodology:

1. The whole atrial endocardium needs to be scrutinized. It will be favored in the future by using computer aid mapping. The incomplete mapping may leave some AF nests predisposing to arrhythmia relapses.

2. Despite the fact that a simplified mapping is possible, currently no device is commercially available specifically for this kind of application.

3. In this series, the value of this technique to ablate AF during arrhythmia was not assessed.

4. Although no more inducing AF, in some cases the triggers may persist being the origin of occasional symptoms.

A present invention provides a new technique for curative radiofrequency AF ablation as described based on the concept and on the demonstration of the compact, of the fibrillar myocardium and of the AF nests. It was observed that the atrial wall is a blend of these two kinds of muscle. Strong evidence that the fibrillar myocardium could be the real AF substratum was found. It could be congenital (atrium-vein transition or myocardium-nervous system transition) or acquired (loose cells originated by degeneration, by stretching or by numerous other processes) and can be found in several parts of the atrial wall and entering the pulmonary veins. The greater the fibrillar/compact myocardium ratio, the greater the frequency and propensity to AF. This tissue, which seems to have intermediate features between nervous and myocardium, can be easily identified and mapped by spectral analysis and phase study. A computer, such as a conventional laptop PC equipped with a processor and memory (see FIG. 20) and using standard Fast Fourier Transform (FFT), was used for this purpose. Elimination or inactivation of the fibrillar myocardium by a low amount of catheter RF application has allowed the PAF cure in 94% and clinical control in 100% of the cases, regardless of the triggers removal or isolation. The procedure is accomplished by transseptal puncture and requires only one catheter for ablation and mapping. RF is applied outside the pulmonary veins, avoiding risk of stenosis. The patient should be in sinus rhythm. However, the spectral analysis may have potential to localize the application targets—AF nests—even during arrhythmia. Taking the inherent care in the transseptal puncture and RF ablation, no complications occur.

What is claimed is:

1. An apparatus, comprising:
an electrophysiology (EP) recording system, including a computer processor, a memory, and a display; and
at least a pair of electrodes coupled through an elongate catheter shaft to the EP recording system, wherein said EP recording system is configured to monitor endocardial signals from at least one atrial wall point having high-density autonomic innervation and adapted to perform endocardial spectral mapping of said endocardial signals and provide a spectral mapping output signal related to the endocardial signals of said wall point, wherein said spectral mapping output signal includes a fractionated spectrum in the frequency domain of a Fourier transform of the spectral mapping output signal.

2. An apparatus according to claim 1, further comprising a handle including a deflection mechanism coupled to a proximal portion of the elongate catheter shaft.

3. An apparatus according to claim 1, wherein a distal portion of the elongate catheter shaft includes an expandable distal mapping portion having a plurality of electrodes coupled thereto.

4. An apparatus according to claim 3, wherein the expandable distal mapping portion comprises a radially-expandable portion.

5. An apparatus according to claim 3, wherein the plurality of electrodes comprises at least ten electrodes.

6. An apparatus according to claim 1, wherein the endocardial spectral mapping is performed during sinus rhythm.

7. An apparatus according to claim 1, wherein the endocardial signal comprises a first endocardial signal and the apparatus further comprises means for measuring a second endocardial signal after an ablation of the myocardium, the second endocardial signal having a fast Fourier transform (FFT) analysis in the frequency domain with a reduction in a number of harmonics compared to an FFT analysis of the first endocardial signal.

8. An apparatus according to claim 7, wherein the second endocardial signal has a reduced signal fractionation characteristic and a left frequency shift compared to the first endocardial signal.

9. An apparatus according to claim 1 further comprising a source of ablation energy operatively coupled to a distal portion of the elongate catheter shaft that, when activated, ablates at least a portion of the at least one atrial wall point such that the activated source of ablation energy one of reduces and eliminates the frequency domain signal of the spectral mapping output signal above about 300 Hz.

10. An apparatus according to claim 9, wherein the portion of the at least one ablated atrial wall point comprises a volume of fibrillar myocardium.

11. An apparatus according to claim 9, wherein the ablation of the myocardium decreases a ratio of a fibrillar myocardium to a compact myocardium of the at least one atrial wall point.

12. An apparatus according to claim 9, wherein the source of ablation energy is activated long enough to achieve at least a portion of cardiac parasympathetic denervation of the at least one atrial wall point.

13. An apparatus according to claim 9, wherein the source of ablation energy comprises an RF generator apparatus adapted to ablate said atrial wall point sufficiently to clinically control at least one of: a neurocardiogenic syncope condition, a functional AV block, a sinus node dysfunction, a carotid sinus syndrome.

14. An apparatus, comprising:
an electrophysiology (EP) recording system, including a computer processor, a memory, and a display;
at least a pair of electrodes coupled through an elongate catheter to the EP recording system, wherein said EP recording system is configured to monitor endocardial signals from a plurality of atrial wall points having high-density autonomic innervation and to perform endocardial spectral mapping of said endocardial signals and provide a spectral mapping output signal related to the endocardial signals of said plurality of wall points, wherein said spectral mapping output signal includes a fractionated spectrum in the frequency domain of a Fourier transform of the spectral mapping output signal, and
a source of ablation energy operatively coupled to a distal portion of the elongate catheter, wherein the elongate catheter is adapted to endocardially ablate a plurality of nerve fibers of at least one of said plurality of atrial wall points sufficient to destroy only a portion of said nerve fibers such that other of said nerve fibers may recover.

15. An apparatus according to claim 14, wherein said elongate catheter is configured to puncture a portion of a transseptal tissue and to perform ablation and mapping of myocardial tissue in a portion of a left atrium.

16. An apparatus according to claim 15, wherein the ablation energy is applied one of around and outside at least one pulmonary vein of the left atrium.

17. An apparatus according to claim 16, wherein the source of ablation is applied in pulses of about 30 Joules to about 40 Joules and wherein the ablation of said at least one atrial wall point is sufficient to clinically control at least one of a neurocardiogenic syncope condition, a functional AV block condition, a sinus node dysfunction, and a carotid sinus syndrome.

18. An apparatus according to claim 17, wherein the source of ablation energy is applied during a period of time of about 15 seconds to about 20 seconds.

19. An apparatus according to claim 18, wherein the spectral mapping output signal includes three frequency channels and wherein the ablation of said at least one atrial wall point is sufficient to clinically control at least one of: a neurocardiogenic syncope condition, a functional AV block, a sinus node dysfunction, and a carotid sinus syndrome.

20. An apparatus according to claim 19, wherein the three frequency channels comprise a first channel of about 30 Hertz (Hz) to about 500 Hz, a second channel of about 100 Hz to about 500 Hz, and a third channel of about 300 Hz to about 500 Hz.

21. An apparatus according to claim 14, further comprising an electroanatomic system, wherein the electroanatomic system and the EP recording system cooperate to localize and display information about a target tissue site including the plurality of nerve fibers, respectively.

22. An apparatus according to 14, wherein the spectral mapping output signal is used to identify at least one of the plurality of atrial wall points having high density autonomic innervation for ablation during one of normal sinus rhythm and an episode of an atrial arrhythmia.

23. A tangible computer-readable medium comprising instructions to cause at least one processor to:
spectral map endocardial signals from at least one atrial wall point having high-density autonomic innervation during one of a normal sinus rhythm condition and a cardiac arrhythmia condition;
obtain an endocardial signal from a volume of myocardium of the at least one atrial wall point; and
identify a fractionated spectrum characteristic in the frequency domain of a Fourier transform of the endocardial signal.

24. A tangible computer-readable medium according to claim 23, wherein the at least one processor controls an ablation process ablating at least a portion of the myocardium of the at least one wall point.

25. A tangible computer-readable medium according to claim 24, wherein the processor controlled ablation process comprises applying an ablation catheter to said at least one atrial wall point to achieve at least some cardiac parasympathetic denervation.

26. A tangible computer-readable medium according to claim 24, wherein the processor controlled ablation process comprises applying a source of ablation energy to said at least one atrial wall point sufficiently to clinically control at least one of a neurocardiogenic syncope condition, a functional AV block, a sinus node dysfunction, or a carotid sinus syndrome.

27. A tangible computer-readable medium comprising instructions to cause at least one processor to control:
mapping of endocardial signals from a plurality of atrial wall points having high density autonomic innervation; and
activating an ablation energy source coupled to a distal portion of a catheter to effectively ablate a plurality of nerve fibers of at least one of said plurality of atrial wall points sufficiently to destroy only a portion of said plurality of nerve fibers such that other of said plurality of nerve fibers may recover.

28. A tangible computer-readable medium according to claim 27, wherein the processor controlled mapping comprises using spectral analysis of fibrillar myocardial tissue and of compact myocardial tissue.

29. A tangible computer-readable medium according to claim 28, wherein the at least one processor processes the spectral analysis to identify the plurality of atrial wall points having high density autonomic innervations for subsequent ablation during atrial fibrillation.

30. A tangible computer-readable medium according to claim 28, wherein the at least one processor specifies the spectral analysis using three frequency channels and wherein the ablation of said at least one atrial wall point is sufficient to clinically control at least one of: a neurocardiogenic syncope condition, a functional AV block, a sinus node dysfunction, or a carotid sinus syndrome.

31. A tangible computer-readable medium according to claim 30, wherein the at least one processor divides the three frequency channels into a first channel of about 30 Hertz (Hz) to about 500 Hz, a second channel of about 100 Hz to about 500 Hz, and a third channel of about 300 Hz to about 500 Hz.

32. A tangible computer-readable medium according to claim 27, wherein the ablation energy application is applied by the at least one processor in pulses of about 30 Joules to about 40 Joules and wherein the ablation energy applied to said at least one atrial wall point is sufficient to clinically control at least one of: a neurocardiogenic syncope condition, a functional AV block condition, a sinus node dysfunction, or a carotid sinus syndrome.

33. A tangible computer-readable medium according to claim 32, wherein the ablation energy is triggered by the at least one processor during a temporal period between about 15 seconds to about 20 seconds.

34. A tangible computer-readable medium according to claim 27, wherein the processor controlled ablation energy source activates during therapy delivery in treating to eliminate arrhythmia.

35. A tangible computer-readable medium comprising instructions to cause one or more computer processors to control:

spectral mapping of endocardial signals from a plurality of atrial wall points having high-density autonomic innervations during sinus rhythm based on cardiac activity signals gathered from endocardial myocardial locations; and an ablation energy application causing necrosis of sufficient nerve fibers of at least one of said plurality of atrial wall points to change the autonomic drive thus enabling a treatment of at least one of: a neurocardiogenic syndrome condition, a functional AV block condition, a sinus node dysfunction, or a carotid sinus syndrome.

36. A tangible computer-readable medium according to claim 35, wherein the processor controlled spectral mapping is performed during a normal sinus rhythm condition.

37. A tangible computer-readable medium according to claim 35, wherein the atrial wall point comprises a volume of fibrillar myocardium.

38. A tangible computer-readable medium according to claim 35, wherein the processor controlled ablation energy application decreases a ratio of the fibril myocardium to the compact myocardium of the at least one atrial wall point.

39. A tangible computer-readable medium according to claim 35, wherein the cardiac activity signals comprise a first endocardial signal and the computer readable medium further comprises instructions to cause the one or more computer processors to measure a second endocardial signal after the ablation energy application, the second endocardial signal having a fast Fourier transform (FFT) in the frequency domain with a reduction in the number of harmonics compared to an FFT of the first endocardial signal.

40. A tangible computer-readable medium according to claim 39, wherein if the second endocardial signal has a reduced fractionation and a left frequency shift compared to the first endocardial signal, the one or more computer processors produces an output signal related to at least one of the reduced fractionation and the left frequency shift.

* * * * *